United States Patent [19]

Bollag et al.

[11] Patent Number: 4,532,355
[45] Date of Patent: Jul. 30, 1985

[54] SUBSTITUTED TRIARYL PHOSPHONIUM DERIVATIVES

[75] Inventors: Werner Bollag, Basel; Rudolf Ruegg, Bottmingen; Gottlieb Ryser, Basel, all of Switzerland

[73] Assignee: Hoffmann-La Roche Inc., Nutley, N.J.

[21] Appl. No.: 417,013

[22] Filed: Sep. 13, 1982

Related U.S. Application Data

[60] Division of Ser. No. 320,775, Nov. 12, 1981, , which is a division of Ser. No. 173,517, Jul. 30, 1980, Pat. No. 4,319,048, which is a division of Ser. No. 037,270, May 9, 1979, Pat. No. 4,224,244, which is a division of Ser. No. 903,438, May 8, 1978, abandoned, which is a division of Ser. No. 714,170, Aug. 13, 1976, Pat. No. 4,105,681, which is a continuation-in-part of Ser. No. 601,148, Aug. 1, 1975, abandoned, which is a continuation-in-part of Ser. No. 454,007, Mar. 22, 1974, abandoned.

[30] Foreign Application Priority Data

Mar. 30, 1973 [CH] Switzerland .......................... 4603/73
Feb. 7, 1975 [CH] Switzerland .......................... 1547/75

[51] Int. Cl.$^3$ .............................................. C07F 9/54
[52] U.S. Cl. .......................................... 568/9; 568/11
[58] Field of Search ........................................ 568/9, 11

[56] References Cited

U.S. PATENT DOCUMENTS

| 1,921,364 | 8/1983 | Lommel et al. ......................... 568/9 |
| 2,703,814 | 3/1955 | Dye, Jr. ................................. 568/9 X |
| 2,946,824 | 7/1960 | Chiddix et al. ......................... 568/9 |
| 3,015,680 | 1/1962 | Isler et al. ........................... 568/9 X |
| 3,065,272 | 11/1962 | Garner et al. ....................... 568/9 X |
| 3,334,144 | 8/1967 | Grisley ................................. 568/9 |
| 3,468,931 | 9/1969 | Franceschi et al. ................ 568/9 X |
| 3,674,854 | 7/1972 | Starnes, Jr. ........................ 568/11 |
| 3,742,064 | 6/1973 | Diamond et al. ...................... 568/9 |
| 3,755,459 | 8/1973 | Diamond ............................... 568/9 |
| 4,251,522 | 2/1981 | Brown ................................. 568/11 |
| 4,272,456 | 6/1981 | Baumann, et al. . |

FOREIGN PATENT DOCUMENTS 1056883 5/1964 United Kingdom .
1173063 12/1969 United Kingdom .

OTHER PUBLICATIONS

Chemical Abstracts 67:101023y (1967).
Chemical Abstracts 78:29334h (1973).
Chemical Abstracts 79:42062h (1973).
Chem. Abstr. 81:120821n (1974).
Carotenoids, Birkhäuser Verlag., 1971, pp. 389–390.
J Org. Chem. 32, 180–184 (1967).
Liebigs Ann. Chem. 1979, 1945–1951.

Primary Examiner—Helen M. S. Sneed
Attorney, Agent, or Firm—Jon S. Saxe; Bernard S. Leon; Elizabeth Manning

[57] ABSTRACT

Novel 9-phenyl 5,6-dimethyl-nona-2,4,6,8-tetraenoic acid,-tetraenal or tetraenol derivatives useful as antitumor agents.

10 Claims, No Drawings

SUBSTITUTED TRIARYL PHOSPHONIUM DERIVATIVES

CROSS REFERENCE TO RELATED APPLICATIONS

This is a division of application Ser. No. 320,775 filed Nov. 12, 1981, which in turn is a division of Ser. No. 173,517 filed July 30, 1980, now U.S. Pat. No. 4,319,048, which in turn is a division of Ser. No. 37,270, filed May 9, 1979, now U.S. Pat. No. 4,224,244, which in turn is a division of Ser. No. 903,438, filed May 8, 1978, now abandoned, which in turn is a division of Ser. No. 714,170, filed Aug. 13, 1976, now U.S. Pat. No. 4,105,681, which in turn is a continuation-in-part of Ser. No. 601,148 filed Aug. 1, 1975, now abandoned, which in turn is a continuation-in-part of Ser. No. 454,007, filed Mar. 22, 1974, now abandoned.

SUMMARY OF THE INVENTION

In accordance with this invention, it has been found that compounds of the formula:

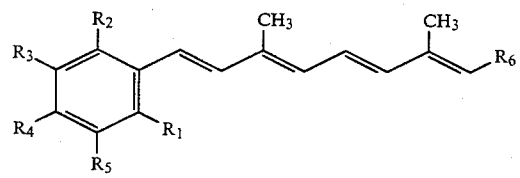

wherein $R_1$ and $R_2$ are lower alkyl; $R_3$ is hydrogen, lower alkyl, lower alkoxy, lower alkenyloxy, nitro, halo, amino, lower alkyl-amino, lower alkanoylamino, or N-heterocyclyl; $R_4$ is hydrogen, lower alkyl, lower alkenyl, lower alkoxy, lower alkenyloxy, nitro, lower alkanoyloxy, amino, lower alkylamino or N-heterocyclyl; $R_5$ is hydrogen, lower alkyl, lower alkenyl, lower alkoxy, lower alkenyloxy, nitro, halo, amino, lower alkanoylamino, lower alkyl amino, or N-heterocyclyl; with the proviso that at least one of $R_3$, $R_4$, and $R_5$ is other than hydrogen; with the further proviso that when $R_3$ or $R_5$ is hydrogen, $R_4$ is other than alkoxy; $R_6$ is formyl, hydroxymethylene, alkoxymethylene, alkanoyloxymethylene, carboxyl, alkoxycarbonyl, alkenloxycarbonyl, alkynyloxycarbonyl, carbamoyl, mono(-lower alkyl)-carbamoyl, di(lower alkyl)-carbamoyl, or N-heterocyclylcarbonyl; or pharmaceutically acceptable salts thereof are useful as anti-tumor agents.

The compounds of formula I are prepared by the reaction of a compound of the formula:

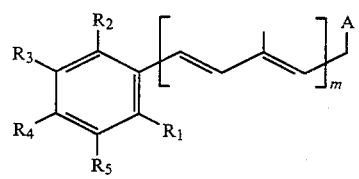

with a compound of the formula:

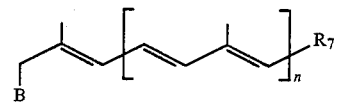

wherein $R_1$, $R_2$, $R_3$, $R_4$ and $R_5$ are as above; m and n are integers of from 0 to 1 with the sum of m and n being equal to 1; one of A or B being oxo and the other being:

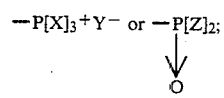

or one of A and B is

and the other being halogen, alkylsulfonyloxy or arylsulfonyloxy; X is aryl; Z is alkoxy; $R_{20}$ is aryl, aralkenyl, aryl substituted with an electron donating or electron withdrawing group or aralkenyl where the aryl moiety is substituted with an electron withdrawing or electron donating group; $R_7$, when B is

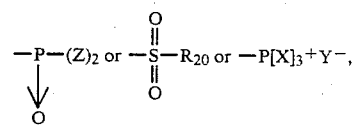

is formyl, carboxy, alkoxycarbonyl, alkenyloxycarbonyl, alkynyloxycarbonyl, di(lower alkyl)carbamoyl or N-heterocyclylcarbonyl; $R_7$, when B is oxo, is carboxy, alkoxymethylene, alkanoyloxymethylene, alkoxycarbonyl, alkenyloxycarbonyl, alkynyloxycarbonyl or N-heterocyclylcarbonyl, $R_7$, when B is halogen, alkylsulfonyloxy or arylsulfonyloxy, is formyl, carboxy, alkoxymethylene, alkanoyloxymethylene, alkoxycarbonyl, alkenyloxycarbonyl; alkynyloxycarbonyl, di(lower alkyl)-amino carbamoyl, or N-heterocyclylcarbonyl, and Y is an anion of an organic or inorganic acid.

In the case where one of A or B form the sulfone group which contains this sulfone group:

This sulfone group in the reaction product can be cleaved to a double bond to form the compound of formula I. In the reaction products of the compound of formula II and III, where $R_7$ is a carboxyl group, this carboxyl group can be esterified or amidated. On the other hand, where $R_7$ is a carboxyl group or an ester group, this reaction product can be reduced to form $R_7$ as a hydroxy group. Where the reaction product contains $R_7$ as a hydroxy group, this group can be esterified or etherified. The resulting alcohol ester can, if derived, be saponified. On the other hand, where $R_7$ in the reaction product is a free hydroxy group or an ester group, this reaction product can be oxidized and form the corresponding compound where $R_7$ is carboxyl, i.e., —COOH.

DETAILED DESCRIPTION

The term "halogen", as utilized in the instant specification, denotes all four halogens, i.e., chlorine, bromide, iodine and fluorine, with chlorine and bromine being preferred. The term "lower alkyl" denotes both straight chain and branched chain lower alkyl groups containing from 1 to 6 carbon atoms such as methyl, ethyl, isopropyl and 2-methylpropyl. The term "lower alkoxy" as used throughout this specification denotes lower alkoxy groups containing from 1 to 7 carbon atoms such as methoxy, propoxy, isopropoxy, ethoxy, etc. The term "lower alkanoyl" denotes lower alkanoyl groups containing from 2 to 6 carbon atoms such as acetyl, propionyl or pivalonyl.

The terms "lower alkenyl" and "lower alkynyl" includes both straight chain and branched chain hydrocarbon groups containing from 2 to 6 carbon atoms such as vinyl, allyl, butenyl, pentenyl, ethynyl, propargyl, butynyl, etc.

The term N-heterocyclyl designates N-heterocyclyl radicals containing preferably 5 or 6 membered rings which contain a nitrogen atom in the ring and which can, if desired, contain a further hetero atom selected from the group consisting of oxygen, nitrogen or sulfur. Among the preferred N-heterocyclyl radicals are included pyrrolidino, pyridino, piperidino, morpholino or thiomorpholino.

The lower alkanoylamino groups contain residues which are derived from lower alkanecarboxylic acids containing from 2 to 6 carbon atoms (e.g. acetic acid, propionic acid or pivalic acid).

The alkoxymethylene and alkoxycarbonyl groups preferably contain alkoxy moieties having from 1 to 6 carbon atoms. These can be straight-chain or branched-chain such as, for example, the methoxy, ethoxy and isopropoxy groups. However, the alkoxy moiety can also be a higher alkoxy group containing from 7 to 20 carbon atoms, especially the cetyloxy group. The alkoxy moiety can be substituted by functional groups; for example, by nitrogen-containing groups such as, for example, by an amino or morpholino group, which may be alkyl-substituted, or by a piperidyl or pyridyl group.

The alkenyloxycarbonyl and alkynyloxycarbonyl groups preferably contain alkenoxy and alkynoxy moieties having from 2 to 6 carbon atoms such as, for example, the allyloxy or propargyloxy group.

The term "alkanoyloxy" designates derivatives of alkanecarboxylic acids containing from 2 to 20 carbon atoms. Among the preferred lower alkanoyloxy groups are included lower alkanoyloxy groups containing from 2 to 6 carbon atoms such as acetyloxy, propionyloxy and pivalyloxy. However, the alkanoyloxy group can be derived from higher alkane carboxylic acids, i.e., acids containing from 6 to 20 carbon atoms such as palmitic acid or stearic acid as well as lower alkanoyloxy groups. The term "alkanoyloxymethylene" denotes alkanoyloxymethylene groups wherein alkanoyloxy is defined as above. Among the preferred alkanoyloxymethylene groups are included acetyloxymethylene and propionyloxymethylene.

The terms "mono" and "di(lower alkyl)carbamoyl" denote mono and di(lower alkyl)carbamoyl radicals wherein lower alkyl is defined as above. Among the preferred mono or di(lower alkyl)carbamoyl groups are included such groups as N-methyl-carbamoyl, N,N-dimethylcarbamoyl, N-isopropylcarbamoyl, and N-tertiarybutylcarbamoyl. The "N-heterocyclylcarbonyl radicals are those which preferably contain a 5 or 6 membered heterocyclic ring, which in addition to the nitrogen atom may contain a further hetero atom selected from the group consisting of nitrogen, oxygen or sulfur. Examples of such N-heterocyclic groups which can be utilized in accordance with this invention are included pyridino, piperidino, morpholino, thiomorpholino and pyrrolidino.

In the compound of formula I, the preferred di(lower alkyl)amino groups denoted are those where the lower alkyl substituent contains from 1 to 4 carbon atoms. Among the preferred lower alkyl amino groups are included ethyl amino, dimethyl amino, diethyl amino and diisopropyl amino. The term lower alkyl amino includes both mono and di-lower alkyl amino groups.

Among the preferred compounds of formula I are the following:

9-(2,3,6-trimethyl-phenyl)-3,7-dimethyl-nona-2,4,6,8-tetraen-1-oic-acid;

9-(2,4,6-trimethyl-phenyl)-3,7-dimethyl-nona-2,4,6,8-tetraen-1-oic acid;

9-(2,4,6-triisopropyl-phenyl)-3,7-dimethyl-nona-2,4,6,8-tetraen-1-oic-acid;

9(2,3,4,6-tetramethyl-phenyl)-3,7-dimethyl-nona-2,4,6,8-tetraen-1-oic acid;

9-(4-methoxy-2,6-dimethyl-phenyl)-3,7-dimethyl-nona-2,4,6,8-tetraen-1-oic-acid;

9-(4-methoxy-2,3,6-trimethyl-phenyl)-3,7-dimethyl-nona-2,4,6,8-tetraen-1-oic acid;

9-(3-methoxy-2,4,6-trimethyl-phenyl)-3,7-dimethyl-nona-2,4,6,8-tetraen-1-oic acid;

9-(4-methoxy-2,3,6-trimethyl-phenyl)-3,7-dimethyl-nona-2,4,6,8-tetraen-1-oic-acid ethyl ester;

9-(4-methoxy-2,3,6-trimethyl-phenyl)-3,7-dimethyl-nona-2-trans, 4-cis, 6-trans, 8-trans-tetraen-1-oic acid ethyl ester;

9-(4-methoxy-2,3,6-trimethyl-phenyl)-3,7-dimethyl-nona-2,4,6,8-tetraen-1-oic acid isopropyl ester;

9-(4-methoxy-2,3,6-trimethyl-phenyl)-3,7-dimethyl-nona-2,4,6,8-tetraen-1-oic acid diethylaminoethyl ester;

9-(4-methoxy-2,3,6-trimethyl-phenyl)-3,7-dimethyl-nona-2,4,6,8-tetraen-1-oic acid amide;

9-(4-methoxy-2,3,6-trimethyl-phenyl)-3,7-dimethyl-nona-2,4,6,8-tetraen-1-oic acid ethyl amide;

9-(4-methoxy-2,3,6-trimethyl-phenyl)-3,7-dimethyl-nona-2,4,6,8-tetraen-1-oic acid allyl ester;

9-(4-methoxy-2,3,6-trimethyl-phenyl)-3,7-dimethyl-nona-2,4,6,8-tetraen-1-oic acid propargyl ester;

9-(3,6-dimethoxy-2,4,5-trimethyl-phenyl)-3,7-dimethyl-nona-2,4,6,8-tetraen-1-oic acid;

9-(4-methoxy-3-allyl-2,6-dimethyl-phenyl)-3,7-dimethyl-nona-2,4,6,8-tetraen-1-oic acid;

9-(4-methoxy-3-nitro-2,6-dimethyl-phenyl)-3,7-dimethyl-nona-2,4,6,8-tetraen-1-oic acid ethyl ester;

9-(3-dimethylamino-2,4,6-trimethyl-phenyl)-3,7-dimethyl-nona-2,4,6,8-tetraen-1-oic acid ethyl ester;

9-(4-isopropoxy-2,3,6-trimethyl-phenyl)-3,7-dimethyl-nona-2,4,6,8-tetraen-1-oic acid;

9-(4-allyloxy-2,3,6-trimethyl-phenyl)-3,7-dimethyl-nona-2,4,6,8-tetraen-1-oic acid;

9-(5-chloro-2,4,6-trimethyl-phenyl)-3,7-dimethyl-nona-2,4,6,8-tetraen-1-oic acid; and 9-(3-nitro-2,4,6-trimethyl-phenyl)-3,7-dimethyl-nona-2,4,6,8-tetraen-1-oic acid.

The toxicity of the compounds of formula I is slight. For example, as will be evident from the following Table, the acute toxicity [$LD_{50}$] of 9-(4-methoxy-2,3,6-trimethyl-phenyl)-3,7-dimethyl-nona-2,4,6,8-tetraen-1-oic acid [A] and of 9-(4-methoxy-2,3,6-trimethyl-phenyl)-3,7-dimethyl-nona-2,4,6,8-tetraen-1-oic acid ethyl ester [B] in mice after intraperitoneal administration in rape-oil lies at 700 or 1000 mg/kg.

TABLE

| | Acute Toxicity | | |
|---|---|---|---|
| | $LD_{10}$ mg/kg | $LD_{50}$ mg/kg | $LD_{90}$ mg/kg |
| Substance A | | | |
| After 1 day | >4000 | >4000 | >4000 |
| After 10 days | 580 | 700 | 890 |
| After 20 days | 580 | 700 | 890 |
| Substance B | | | |
| After 1 day | >4000 | >4000 | >4000 |
| After 10 days | 1400 | 1900 | 2600 |
| After 20 days | 710 | 1000 | 1400 |

The compounds of formula I are effective for utilizing tumors such as papillomas. In the papilloma test, tumors induced with dimethylbenzanthracene and croton oil regress. The diameters of the papillomae decline within 2 weeks on intraperitoneal administration. In the case of substance A, the decline is by 38% at 50/mg/kg/week and by 69% at 100 mg/kg/week and in the case of substance B the decline is by 45% at 25 mg/kg/week and by 63% at 50 mg/kg/week.

The compounds of formula I are also useful as medicaments for the topical and systemic therapy of acne, psoriasis and other related dermatological disorders which are characterized by an increased or pathologically altered cornification, as well as inflammatory and allergic dermatological conditions. They can also be used to treat disorders which are characterized by inflammatory or degenerative alterations of the mucous membranes.

The polyene compounds of formula I can accordingly be used as medicaments; for example, in the form of pharmaceutical preparations which contain them in association with a compatible pharmaceutical carrier. The pharmaceutical preparations serving for systemic application can, for example, be produced by adding a polyene compound of formula I as the active ingredient to non-toxic, inert, solid or liquid carriers which are usual in such preparations. The pharmaceutical preparations can be administered enterally or parenterally. Suitable pharmaceutical preparations for enteral administration are, for example, tablets, capsules, dragees, syrups, suspensions, solutions and suppositories. Pharmaceutical preparations in the form of infusion or injection solutions are suitable for parenteral adminstration.

The dosages in which the polyene compounds of formula I can be administered can vary according to the mode of administration and route of administration as well as according to the requirements of the patient.

The polyene compounds of formula I can be administered in amounts of from 5 mg. to 200 mg. daily in one or more dosages. Capsules with a content of a ca 10 mg. to ca 100 mg. of a polyene compound are a preferred form of presentation.

The pharmaceutical preparations can contain inert or other pharmacodynamically active additives. Tablets or granules, for example, can contain a series of binding agents, fillers, carrier materials or diluents. Liquid preparations can, for example, take the form of a sterile water-miscible solution. Besides the polyene compounds of formula I, capsules can additionally contain a filling material or thickening agent. Furthermore, flavor-improving additives as well as the substances usually used as preserving, stabilizing, moisture-retaining or emulsifying agents, salts for varying the osmotic pressure, buffers and other additives can be present.

The carrier materials and diluents mentioned hereinbefore can be organic or inorganic substances; for example, water, gelatin, lactose, starches, magnesium stearate, talcum, gum arabic, polyalkyleneglycols and the like. It is of course a prerequisite that all adjuvants used in the production of the pharmaceutical preparations are non-toxic.

For topical administration, the polyene compounds of formula I are expediently made up in the form of ointments, tinctures, creams, solutions, lotions, sprays, suspension and the like. Ointments and creams, as well as solutions, are preferred. These pharmaceutical preparations intended for topical administration can be produced by mixing the polyene compounds as the active ingredient with non-toxic, inert solid or liquid carriers suitable for topical administration which are usual per se in such preparations.

Expedient for topical administration are ca 0.01% to ca 0.3% (preferably 0.02% to 0.1%) solutions as well as ca 0.05% to ca 5% (preferably ca 0.1% to ca 2.0%) ointments or creams.

An antioxidant (e.g. tocopherol, N-methyl-γ-tocopheramine, butylated hydroxyanisole or butylated hydroxytoluene can optionally be added to the pharmaceutical preparations.

The aryl groups denoted by X in the triarylphosphonium groups of the formula $-P[X]_3{}^+Y^-$ in the compounds of formula II or III include all generally known aryl groups, but especially mononuclear aryl groups such as phenyl, lower alkyl-substituted phenyl or lower alkoxy-substituted phenyl (e.g. tolyl, xylyl, mesityl and p-methoxyphenyl). Of the inorganic acid anions denoted by Y, the chloride, bromide, iodide and hydrosulphate ions are preferred and, of the organic acid anions, the tosyloxy ion is preferred.

The alkoxy groups denoted by Z in the dialkoxyphosphinyl groups of the formula

are preferably lower alkoxy groups containing from 1 to 6 carbon atoms, especially methoxy and ethoxy.

The preferred electron withdrawing groups are those which are weakly electron withdrawing. Examples of aryl and aralkenyl groups, which may be substituted by one or more electron donating to weakly electron-withdrawing substituents, denoted by $R_{20}$ in the sulfone group of the formula:

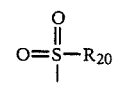

wherein $R_{20}$ is as above; are phenyl and styryl which may be substituted in the o-, m- or p-position by methoxy, phenoxy, acetoxy, dimethylamino, phenylmethylamino, acetylamino, thiomethyl, thiophenyl, thioacetyl, chloro, bromo or cyano or in the m-position by nitro.

The starting materials of formulae II and III are, in part, novel compounds.

Compound of formula II where m is 0 and A is a triarylphosphonium group have the following formula:

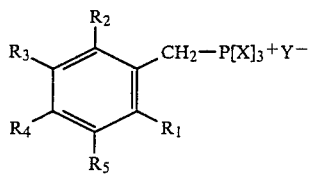
II-a wherein $R_1$, $R_2$, $R_3$, $R_4$, $R_5$, X and Y are as above.

Compounds of the formula II where m is 0 and A is a dialkoxy phosphnyl group have the following formula:

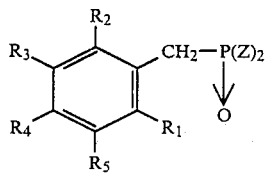
II-c wherein $R_1$, $R_2$, $R_3$, $R_4$, $R_5$ and Z are as above. The compounds of formula II-a and II-c can be prepared, for example, by treating a corresonding ($R_1$-$R_5$) substituted-benzene with formaldehyde in the presence of a hydrohalic acid (e.g. concentrated hydrochloric acid), if desired in a solvent (especially glacial acetic acid) to prepare a compound of formula II where m is 0 and A is a halogen, i.e., the compound of formula II-i. The halide of formula II-i is reacted in a converted manner with a triaryl phosphine in a solvent, preferably with triphenyl phosphine in toluene or benzene, or with a trialkyl phosphite, especially with triethyl phosphite.

An alkoxy group present in the aforementioned ($R_1$-$R_5$)-benzene can be introduced, for example, by alkylation of a hydroxy group present. For example, the corresponding phenol can be reacted, preferably in a solvent (e.g. an alkanol) and in the presence of a base (e.g. potassium carbonate), with an alkyl halide (e.g. methyl iodide) or dimethyl sulphate.

Compounds of formula II where m is 1 and A is a triaryl phosphonium group have the formula:

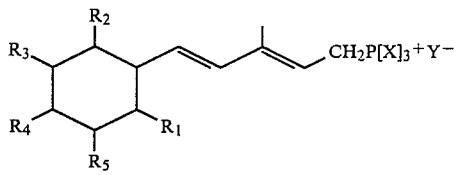
II-b wherein $R_1$, $R_2$, $R_3$, $R_4$, $R_5$, X and Y are as above. Compounds of formula II where m is 1 and A is dialkoxyphosphinyl have the formula:

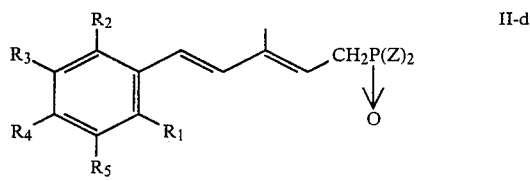
II-d wherein $R_1$, $R_2$, $R_3$, $R_4$, $R_5$ and Z is as above. The compounds of formula II-b and II-d can be prepared by first formylating the corresponding ($R_1$-$R_5$)-benzene. This can be carried out, for example, by formylating the ($R_1$-$R_5$) substituted-benzene in the presence of a Lewis acid. As the formylating agent there can be used, in particular, an orthoformic acid ester, formyl chloride and dimethylformamide. Especially suitable Lewis acids are the halides of zinc, aluminium, titanium, tin and iron such as zinc chloride, aluminium trichloride, titanium tetrachloride, tin tetrachloride and iron trichloride as well as the halides of inorganic and organic acids such as, for example, phosphorus oxychloride and methane sulfochloride.

If the formylating agent is present in excess, the formylation may be carried out without the addition of a further solvent. In general, however, it is recommended to carry out the formylation in an inert solvent (e.g. nitrobenzene or in a chlorinated hydrocarbon such as methylene chloride). The formylation can be carried out at a temperature between 0° C. and the boiling point of the mixture.

A resulting ($R_1$-$R_5$)-benzaldehyde can subsequently be chain-lengthened in a conventional manner by condensation with acetone in the cold (i.e. at a temperature of about 0°–30° C.) in the presence of alkali (e.g. dilute aqueous sodium hydroxide to give a ($R_1$-$R_5$)-phenyl-but-3-en-2-one which can be converted into the corresponding ($R_1$-$R_5$)-phenyl-3-methyl-3-hydroxy-penta-4-en-1-yne in a manner known per se by means of an organometallic reaction (e.g. by means of a Grignard reaction by the addition of acetylene). The resulting tertiary ethylenic carbinol can subsequently be partially hydrogenated in a conventional manner using a partially deactivated noble metal catalyst (lindlar catalyst). The resulting tertiary ethylenic carbinol can subsequently be converted, under allyl rearrangement, into the desired phosphonium salt of formula II-b where m stands for 1 by treatment with a triaryl phosphine, especially with triphenyl phosphine, in the presence of a hydrohalide such as hydrogen chloride or hydrogen bromide in a solvent (e.g. in benzene). The tertiary ethylenic carbinol can, moreover, be halogenated to give the compound of formula II where m is 1 and A is a halide, i.e. the compound of formula II-k. This halide of formula II-k can be reacted with a trialkyl phosphite (e.g. triethyl phosphite) to give a corresponding phosphonate of formula II-d.

Compounds of formula II where m is 0 and A is a sulfone group have the formula:

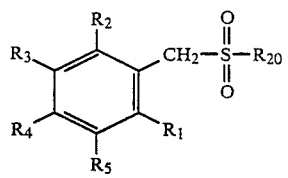
II-e wherein $R_1$, $R_2$, $R_3$, $R_4$, $R_5$ and $R_{20}$ are as above. Compounds of formula II-e can be prepared, for example, by dissolving a ($R_1$–$R_5$)-phenol or a corresponding halobenzene in a polar solvent such as an alcohol (e.g. methanol, ethanol or isopropanol) or in tetrahydrofuran or dimethylformamide or in glacial acetic acid and treating the solution at room temperature with a sulfinic acid of the formula:

wherein $R_{20}$ is as above, or with an alkali salt thereof. The sulfone can be isolated, for example, by making the reaction mixture neutral by adding an aqueous sodium hydrogen carbonate solution and extracting the sulfone with an organic solvent (e.g. ethyl acetate or ether).

Compounds of formula II where m is 1 and A is a sulfone group having the formula:

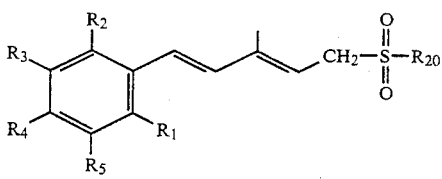

wherein $R_1$, $R_2$, $R_3$, $R_4$, $R_5$ and $R_{20}$ are as above. Compounds of formula II-f can be prepared in an analogous manner by reacting a ($R_1$–$R_5$)-phenyl-3-methyl-penta-2,4-dien-1-ol or a halide thereof with a sulfinic acid as set forth hereinabove or with an alkali salt thereof.

Compounds of formula II where m is zero and A is oxo, i.e., the compound of formula II-g can be prepared, for example, by formylating in the previously described manner a ($R_1$–$R_5$)-benzene. In this manner, a ($R_1$–$R_5$)-benzaldehyde is directly obtained from the ($R_1$–$R_5$) benzene.

Compounds of formula II where m is 1 and A is oxo, i.e., the compound of formula II-h can be prepared, for example, by submitting a ($R_1$–$R_5$)-phenyl-but-3-en-2-one, described hereinbefore in connection with the preparation of compounds of formula II-b, to a Wittig reaction with ethoxycarbonyl-methylenetriphenylphosphorane or with diethyl-phosphonoacetic acid ethyl ester. The resulting ($R_1$–$R_5$)-phenyl-3-methyl-penta-2,4-dien-1-oic acid ethyl ester is subsequently reduced in the cold with a mixed metal hydride, especially lithium aluminium hydride, in an organic solvent (e.g. diethyl ether or tetrahydrofuran) to give a ($R_1$–$R_5$)-phenyl-3-methyl-penta-2,4-dien-1-ol. This alcohol is then oxidized by treatment with an oxidizing agent, for example, with manganese dioxide in an organic solvent such as acetone or methylene chloride at a temperature between 0° C. and the boiling point of the mixture to give the desired ($R_1$–$R_5$)-phenyl-3-methyl-penta-2,4-dien-1-al of formula II-h.

The compounds of formula III are also, in part, novel.

Compounds of formula III where n is zero and B is a triarylphosphonium group [III-a] or a dialkoxyphosphinyl group [III-c] can be readily prepared by reacting an optionally esterified 3-halomethyl-crotonic acid or an etherified 3-halomethyl-crotyl alcohol with a triaryl phosphine in a solvent, preferably with triphenyl phosphine in toluene or benzene, or with a trialkyl phosphite, especially with triethyl phosphite.

Compounds of formula III where n is 1 and B is a triarylphosphonium group [III-b] or a dialkoxyphosphinyl group [III-d] can be prepared, for example, by reducing the formyl group of an aldehyde of formula III-h in which n stands for 1 to the hydroxymethyl group using a metal hydride such as sodium borohydride in an alkanol (e.g. ethanol or isopropanol). The resulting alcohol can be halogenated using a conventional halogenating agent (e.g. phosphorus oxychloride) and the resulting 8-halo-3,7-dimethyl-octa-2,4,6-triene-1-carboxylic acid (a halide of formula III in which n stands for 1 and B is halogen) or a derivative thereof can be reacted either with a triaryl phosphine in a solvent, preferably with triphenyl phosphine in toluene or benzene, to give a desired phosphonium salt of formula III-b or with a trialkyl phosphite, especially with triethyl phosphite, to give a desired phosphonate of formula III-d.

Compounds of formula III-e where n is zero and B is a sulfone group can be prepared, for example, by reacting 4-hydroxy-3-methyl-but-2-en-1-al or the corresponding acetate or bromide in a polar solvent (e.g. isopropanol or n-butanol) in the manner previously described with one of the sulfinic acids defined hereinbefore or with an alkali metal salt thereof.

Compounds of formula III-f where n is 1 and B is a sulfone group can be prepared in a manner analogous to that described earlier by the reaction of, for example, 8-hydroxy-3,7-dimethyl-octa-2,4,6-trien-1-oic acid or the corresponding acetate or bromide of this alcohol with a sulfinic acid as hereinbefore defined or with an alkali metal salt thereof.

Compounds of formula III-g where n is zero and B is an oxo group can be prepared, for example, by oxidatively cleaving an optionally esterified tartaric acid; for example, using lead tetraacetate at room temperature in an organic solvent such as benzene. The resulting glyoxalic acid derivative is subsequently condensed in a manner known per se, conveniently in the presence of an amine, with propionaldehyde at an elevated temperature (e.g. at a temperature between 60° C. and 110° C.) with water cleavage to give the desired 3-formyl-crotonic acid derivative.

Compounds of formula III-h where n is 1 and B is an oxo group can be prepared, for example, by reacting 4,4,-dimethoxy-3-methyl-but-1-en-3-ol with phosgene in the cold, preferably at −10° C. to −20° C., in the presence of a tertiary amine such as pyridine and condensing the resulting 2-formyl-4-chloro-but-2-ene under conditions of a Wittig reaction with an optionally esterified 3-formyl-crotonic acid or to an optionally esterified or etherified 3-formyl-crotyl alcohol to give the desired aldehyde of formula III-b.

According to the process provided by the present invention, the following reactions are effected:
phosphonium salts of formula II-a or II-b are reacted with aldehydes of formula III-h or III-g, or
phosphonium salts of formula III-a or III-b are reacted with aldehydes of formula II-h or II-g, or
phosphonates of formula II-c or II-d are reacted with aldehydes of formula III-h or III-g, or
phosphonates of formula III-c or III-d are reacted with aldehydes of formula II-h or II-g, or
sulfones of formula II-e or II-f are reacted with halides of formula III-k or III-i, or sulfones of formula III-e or III-f are reacted with halides of formula II-k or II-i.

According to the Wittig procedure, the reaction components are reacted with one another in the presence of an acid binding agent, for example, in the presence of an alkali metal alcoholate such as sodium methylate or in the presence of an optionally alkyl-substituted alkylene oxide, especially in the presence of ethylene oxide or 1,2-butylene oxide, if desired in a solvent (e.g. in a chlorinated hydrocarbon such as methylene chloride or in dimethylformamide) at a temperature between room temperature and the boiling point of the reaction mixture.

According to the Horner procedure, the reaction components are reacted with one another with the aid of a base and preferably in the presence of an inert organic solvent; for example, with the aid of sodium hydride in benzene, toluene, dimethylformamide, tetrahydrofuran, dioxan or 1,2-dimethoxyethane or with the aid of an alkali metal alcoholate in an alkanol (e.g. sodium methylate in methanol) at a temperature between 0° C. and the boiling point of the reaction mixture.

According to the Julia procedure, the reaction components are reacted with one another with the aid of a condensation agent, conveniently in the presence of a polar solvent. Suitable solvents are, for example, dimethylformamide, dimethyl sulphoxide, dimethylacetamide, tetrahydrofuran and hexamethylphosphoric acid triamide as well as alkanols such as methanol, isopropanol or tertbutanol. Examples of strong bases which are preferably used as the condensation agent are alkali metal carbonates (especially sodium carbonate), alkaline earth metal carbonates, alkali metal hydroxides (e.g. sodium hydroxide or potassium hydroxide), alkali metal alcoholates (e.g. sodium methylate and, especially, potassium tertbutylate), alkaline earth metal alcoholates, alkali metal hydrites (e.g. sodium hydride), alkyl-magnesium halides (e.g. methyl-magnesium bromide) and alkali metal amides (e.g. sodium amide). The reaction is expediently carried out at a low temperature, esepecially at a temperature below the freezing point (e.g. between $-50°$ C. and $-80°$ C.).

It has been shown to be convenient in certain cases to carry out the reactions described hereinbefore in situ; i.e. without isolating the phosphonium salt, phosphonate or sulfone from the medium in which it is prepared.

A carboxylic acid of formula I can be converted in a manner known per se (e.g. by treatment with thionyl chloride, preferably in pyridine) into an acid chloride which can be converted by treatment with ammonia into an amide and by reaction with an alkanol into an ester.

A carboxylic acid ester of formula I can be hydrolysed in a manner known per se (e.g. by treatment with an alkali, especially aqueous-alcoholic sodium hydroxide or potassium hydroxide) at a temperature between room temperature and the boiling point of the mixture and then amidated either via an acid halide or as described hereinafter.

A carboxylic acid ester of formula I can be converted directly into a corresponding amide, for example, by treatment with lithium amide. The lithium amide is advantageously treated with the ester at room temperature.

A carboxylic acid or a carboxylic acid ester of formula I can be reduced in a manner known per se to give a corresponding alcohol of formula I. The reduction is advantageously carried out using a metal hydride or alkyl metal hydride in an inert solvent. The preferred hydrides are the mixed metal hydrides such as lithium aluminium hydride or bis[methoxy-ethylenoxy]-sodium aluminium hydride. Suitable solvents are, inter alia, ether, tetrahydrofuran or dioxan when lithium aluminium hydride is used and ether, hexane, benzene or toluene when diisobutyl aluminium hydride or bis[methoxyethylenoxy]-sodium aluminium hydride is used.

An alcohol of formula I can be etherified with an alkyl halide (e.g. ethyl iodide), for example, in the presence of a base, preferably sodium hydride, in an organic solvent such as dioxan, tetrahydrofuran, 1,2-dimethoxyethane, dimethylformamide or in the presence of an alkali metal alcoholate in an alkanol at a temperature between 0° C. and room temperature.

An alcohol of formula I can also be esterified by treatment with an alkanoyl halide or anhydride, expediently in the presence of a base (e.g. pyridine or triethylamine) at a temperature between room temperature and the boiling point of the mixture.

An alcohol ester can be saponified in a manner known per se; for example, in the manner previously described in connection with the hydrolysis of a carboxylic acid ester.

An alcohol of formula I or an ester thereof can be oxidized in a manner known per se to give a corresponding acid of formula I. The oxidation is advantageously carried out with silver (I) oxide and alkali in water or in an organic water-miscrible solvent at a temperature between room temperature and the boiling point of the mixture.

An amine of formula I forms addition salts with inorganic and organic acids. Examples of such salts are those formed with hydrohalic acids (especially with hydrochloric or hydrobromic acid), with other mineral acids (e.g. with sulphuric acid) and with organic acids (e.g. with benzoic acid, acetic acid, citric acid or lactic acid).

A carboxylic acid of formula I forms salts with bases, especially with alkali metal hydroxides and especially with sodium hydroxide or potassium hydroxide.

The compounds of formula I can occur as cis/trans mixtures which, if desired, can be separated into the cis and trans components or isomerised to the all-trans compounds in a manner known per se.

The following examples are illustrative but not limitative of this invention. In the examples, the ether utilized was diethyl ether. In the examples concentrated hydrochloric acid denotes an aqueous solution containing about 37% by weight hydrochloric acid. The term 35% formaldehyde which appears in the Examples indicates an aqueous solution containing 35% formaldehyde. The term "low boiling petroleum ether" as used in the examples designates petroleum ether boiling at 0° C.

The sodium hydride (50–60%) utilized in the examples refers to a mineral oil suspension containing 30 to 60% by weight sodium hydride.

EXAMPLE 1

228 g of 5-(4-methoxy-2,3,6-trimethyl-phenyl)-3-methyl-penta-2,4-diene-1-triphenylphosphonium bromide are introduced under nitrogen gassing into 910 ml of dimethylformamide and treated with cooling at 5°–10° C. within 20 minutes with 17.5 g of a suspension of sodium hydride (about 50% by weight) in mineral oil. The mixture is stirred for 1 hour at about 10° C., then treated at 5°–8° C. dropwise with 61.8 g of 3-formylcrotonic acid butyl ester, heated for 2 hours at 65° C., subsequently introduced into 8 l of ice-water and, after the addition of 300 g of sodium chloride, thoroughly extracted with a total of 18 l of hexane. The extract is washed 5 times with 1 l of methanol/water (6:4 parts by volume) each time and 2 times with 1.5 l of water each time, dried over sodium sulphate and evaporated under reduced pressure to leave 9-(4-methoxy-2,3,6-trimethyl-phenyl)-3,7-dimethyl-nona-2,4,6,8-tetraen-1-oic acid butyl ester, m.p. 80°–81° C. as the residue.

EXAMPLE 2

125.8 g of 9-(4-methoxy-2,3,6-trimethyl-phenyl)-3,7-dimethyl-nona-2,4,6,8-tetraen-1-oic acid butyl ester are introduced into 2000 ml of abs. ethanol and treated with a solution of 125.8 g of potassium hydroxide in 195 ml of water. The mixture is heated to boiling under nitrogen gassing for 30 minutes, then cooled, introduced into 10 l of ice-water and, after the addition of about 240 ml of conc. hydrochloric aid [pH 2–4], thoroughly extracted with a total of 9 l of methylene chloride. The extract is washed with about 6 l of water to neutrality, dried over calcium chloride and evaporated under reduced pressure. The residue is taken up in 700 ml of hexane. The precipitated 9-(4-methoxy-2,3,6-trimethyl-phenyl)-3,7-dimethyl-nona-2,4,6,8-tetraen-1-oic acid melts at 228°–230° C.

EXAMPLE 3

500 g of 2,3,5-trimethylphenol are introduced into 1840 ml of ethanol and 184 ml of water and treated, with gentle stirring, with 240 g of potassium hydroxide. To the resulting clear solution, there are added dropwise at 0°–5° C. within 30–45 minutes 626 g of methyl iodide. The reaction mixture is stirred for 2 hours at room temperature, subsequently stirred under reflux conditions for 12 hours at 60° C., then treated with 5 l of water and thoroughly extracted with a total of 6 l of diethyl ether. The extract is washed first with 3 l of 3 aqueous sodium hydroxide, then washed 2 times with 1 l of water each time, dried over sodium sulphate and evaporated under reduced pressure. The remaining 2,3,5-trimethylanisole, after rectification, boils at 88°–90° C./10 mm Hg.

184 g of phosphorus oxychloride are added dropwise to 87.1 g of dimethylformamide with stirring at 10°–20° C. within 20–30 minutes. The temperature should rise to 25° C. towards the end of the addition. Into the obtained mixture, there are introduced 150 g of 2,3,5-trimethylanisole within 20 minutes with cooling at 10°–20° C. The reaction mixture is slowly heated up to max. 115° C., stirred for 6 hours at 100° C. for the completion of the reaction, poured, after cooling, into 2 kg of ice/water 1:1 parts by volume and, after the addition of 1500 ml of benzene, treated with 500 g of sodium acetate. The water phase which forms is separated after stirring for 1 hour and again extracted with 1000 ml of benzene. The combined benzene extracts are washed successively with 480 ml of 1.5 aqueous hydrochloric acid and 500 ml of water, dried over sodium sulphate and filtered over 20 g of decoloring carbon. The filtrate is evaporated under reduced pressure. The remaining 2,3,6-trimethyl-p-anisaldehyde melts, after recrystallisation from hexane at 65°–66° C.

260 g of 2,3,6-trimethyl-p-anisaldehyde are introduced into a mixture of 3500 ml of acetone and 1400 ml of water and treated with 730 ml of 10 wt.% aqueous sodium hydroxide with stirring at 0°–5° C. in the course of about 30 minutes. The mixture is stirred for 3 days at room temperature and subsequently, after lowering of the pH value to 4–5 by addition of acetic acid, concentrated under reduced pressure. The concentrate is extracted with a total of 3000 ml of diethyl ether. The ether extract is washed first with 700 ml of an aqueous 5% by weight sodium bicarbonate solution, then washed with 700 ml of water, dried over sodium sulphate and evaported under reduced pressure. The remaining oily 4-(4-methoxy-2,3,6-trimethyl-phenyl)-but-3-en-2-one boils, after rectification, at 120°–127° C./0.05 mm Hg.

36.45 g of magnesium are superficially corroded with a small amount of iodine, introduced into 1000 ml of tetrahydrofuran and treated dropwise with 162.5 g of ethyl bromide under nitrogen within 45 minutes. In so doing, the temperature should amount initially to 8°–10° C. It can rise to 25° C. towards the end of the introduction. The reaction mixture is stirred, optionally with renewed addition of a further 5–10 ml of alkyl bromide, until the magnesium has gone completely into solution. The obtained Grignard solution is subsequently added dropwise at 0° C. into a saturated acetylene/tetrahydrofuran solution manufactured from 650 ml of tetrahydrofuran by gassing for 3 hours with acetylene at −10° to −5° C. The reagent is stirred for 1 hour at 0° C., then treated dropwise within 30–45 minutes with acetylene gassing at 0° C., with a solution of 218 g of 4-(4-methoxy-2,3,6-trimethyl-phenyl)-but-3-en-2-one in 250 ml of tetrahydrofuran. The reaction mixture is stirred for 24 hours at 0° C. and subsequently for 12 hours at room temperature, then introduced into 4.5 kg of ice/water 3.5:1 parts by volume, adjusted to a pH of about 4 by the addition of 700 ml of 3N hydrochloric acid and thoroughly extracted with a total of 3 l of diethyl ether. The ether extract is washed to neutrality with a total of 2 l of water, dried over sodium sulphate and filtered over 20 g of decoloring carbon. The Nitrate is evaporated under reduced pressure, the remaining 5-(4-methoxy-2,3,6-trimethylphenyl)-3-methyl-3-hydroxy-penta-4-en-1-yne, after rectification at 125°–135° C./0.04 mm Hg, melts at 58°–60° C.

244 g of 5-(4-methoxy-2,3,6-trimethyl-phenyl)-3-methyl-3-hydroxy-penta-4-en-1-yne are dissolved in 400 ml of hexane and, after the addition of 45 g of a partially poisoned palladium catalyst, hydrogenated at room temperature under normal pressure. The hydrogenation is stopped after about 40–60 minutes after the uptake of the amount of hydrogen necessary for the saturation of the acetyleneethylene bond[25 l]. The hydrogenation solution is filtered. The filtrate is washed with 300 ml of ethyl acetate and evaporated under reduced pressure. The remaining 5-(4-methoxy-2,3,6-trimethyl-phenyl)-3-methyl-3-hydroxy-pent-1,4-diene melts at 46°–47° C.

246 g of 5-(4-methoxy-2,3,6-trimethyl-phenyl)-3-methyl-3-hydroxy-penta-1,4-diene are dissolved in 2400 ml of benzene. The solution is treated with 343 g of triphenylphosphonium hydrobromide, stirred for 24 hours at 60° C., then cooled and the benzene separated. The sediment is digested 4 times with 500 ml of benzene each time and, after separation of the benzene washings, dissolved in 700 ml of methylene chloride. The solution is evaporated under reduced pressure. The remaining 5-(-4-methoxy-2,3,6-trimethyl-phenyl)-3-methyl-penta-2,4-diene-1-triphenylphosphonium bromide is dried in vacuo before further processing.

EXAMPLE 4

1775 g of lead tetraacetate (90%) are gradually introduced within 30 minutes at 25°–30° C. into a solution of 1000 g of L(+)-tartaric acid dibutyl ester in 3850 ml of benzene. The reaction mixture is subsequently stirred for 1 hour at room temperature. The sediment is filtered off and extracted with 500 ml of benzene. The benzene extract is evaporated under reduced pressure. The remaining glyoxalic acid butyl ester boils, after rectification, at 50°–65° C./12 mm Hg.

836 g of the obtained glyoxalic acid butyl ester are introduced into 376 g of propionaldehyde. The mixture is treated dropwise at 60° C. with 40.8 g of di-n-butylamine. In so doing, the reaction temperature should not rise higher than 106° C. The reaction mixture is then stirred for 2 hours at 116°–111° C., cooled and taken up in ether. The diethyl ether extract is washed successively with 500 ml of 1N sulphuric acid, 700 ml of water, 1000 ml of 5% by weight aqueous sodium bicarbonate solution and subsequently with 1000 ml of water, dried over sodium sulphate and evaporated under reduced pressure. The remaining 3-formyl-crotonic acid butyl ester boils, after rectification, at 93°–105° C./14 mm Hg; $n_D^{25} = 1$.

EXAMPLE 5

28.5 g of 5-(4-methoxy-2,3,6-trimethyl-phenyl)-3-methyl-penta-2,4-diene-1-triphenylphosphonium bromide are introduced under nitrogen gassing into 240 ml of isopropyl alcohol. After the addition of 0.12 g of butylated hydroxy toluene, the mixture is cooled to −35° C. and treated at this temperature under strong stirring within 5 minutes with 7.50 g of 3-formylcrotyl acetate. The reaction mixture is subsequently mixed with 7.2 g of a 50 wt.% aqueous potassium hydroxide solution—in so doing the temperature should not rise above −25° C.—and, after stirring for 1 hour at −30° C., introduced into a mixture of 110 g of water, 90 g of ice and 90 ml of hexane. The hexane layer is separated. The aqueous phase is shaken out 5 times with 90 ml of hexane each time. The combined hexane extracts are shaken out 5 times with 180 ml of methanol/water 80:20 parts by volume each time. The hexane phase is washed with water, dried over sodium sulphate and evaporated under reduced pressure. The remaining 1-acetoxy-9-(4-methoxy-2,3,6-trimethyl-phenyl)-3,7-dimethyl-nona-2,4,6,8-tetraene, an oil, can be purified by absorption on silica gel eluent: hexane/diethyl ether 80:20 parts by volume.

EXAMPLE 6

59 g of 2,3,6-trimethyl-benzyl-triphenylphosphonium bromide and 28 g of 7-formyl-3-methyl-octa-2,4,6-trien-1-oic acid butyl ester are introduced into 280 ml of abs. ethanol. The mixture is treated dropwise at a temperature between 0° and 10° C. with a solution of 2.72 g of sodium in 160 ml of abs. ethanol, subsequently stirred for 48 hours at room temperature, then introduced into 800 ml of water and thoroughly extracted with a total of 3000 ml of hexane. The hexane extract is shaken out 3 times with 1000 ml of methanol/water 60:40 parts by volume each time, then dried over sodium sulphate and evaporated under reduced pressure. The remaining 9-(2,3,6-trimethyl-phenyl)-3,7-dimethyl-nona-2,4,6,8-tetraen-1-oic acid butyl ester is an oil.

EXAMPLE 7

10 g of 9-(2,3,6-trimethyl-phenyl)-3,7-dimethyl-nona-2,4,6,8-tetraen-1-oic acid butyl ester are introduced into 100 ml of abs. ethanol and, after the addition of a solution of 10 g of potassium hydroxide in 20 ml of water, heated to boiling under nitrogen gassing. The initially cloudy solution becoming clear when boiling is cooled after 30 minutes and introduced into ice-water. The reaction solution is thoroughly extracted, after acidification with conc. hydrochloric acid, with methylene chloride. The extract is washed to neutrality with water, dried over calcium chloride and evaporated under reduced pressure. The remaining 9-(2,3,6-trimethyl-phenyl)-3,7-dimethyl-nona-2,4,6,8-tetraen-1-oic acid melts, after recrystallisation from ethyl acetate, at 191°–192° C.

EXAMPLE 8

300 g of pseudocumol are treated dropwise with 700 ml of conc. sulphuric acid. In so doing, the temperature can rise to 40° C. The mixture is subsequently cooled to 20° C. and, after the addition of 450 g of bromine, stirred for 1 hour at room temperature. Thereafter, 700 ml of water are added dropwise. In so doing, the temperature rises to 50° C. The precipitated mixture of solid materials is filtered off and dissolved in 3000 ml of hot water. The insoluble 3,5,6-tribromo-1,2,4-trimethylbenzene is separated and rejected. The aqueous solution is slowly introduced into 1000 ml of 80 wt.% sulphuric acid which is being heated at 180° C. and blown through with steam. The 1-bromo-2,3,6-trimethylbenzene coming over with the steam boils at 86° C./6 mm Hg.

250 g of 1-bromo-2,3,6-trimethylbenzene are dissolved in 400 ml of diethyl ether. The solution is added dropwise at 20°–30° C. with gentle cooling into a suspension of 66.5 g of magnesium (activated with iodine) and 200 ml of diethyl ether. The mixture is treated dropwise at 20°–30° C. with a solution of 135 g of ethyl bromide in 250 ml of diethyl ether and subsequently heated to boiling under reflux conditions for 3–4 hours. As soon as the magnesium has gone into solution, 385 g of orthoformic acid ethyl ester dissolved in 250 ml of abs. diethyl ether are introduced. The reaction mixture is heated to boiling for 5 hours, after evaporation of the diethyl ether poured onto ice, treated with 1000 ml of 5N hydrochloric acid and heated to boiling for 30 minutes under carbon dioxide gassing. The distillate, obtainable thereafter by water distillation, is extracted with methylene chloride. The methylene chloride phase is evaporated under reduced pressure. The remaining 2,3,6-trimethylbenzaldehyde boils at 70°–72° C./1.2 mm Hg.

129.6 g of 2,3,6-trimethylbenzaldehyde are dissolved in 300 ml of methanol and, after the addition of 70 ml of water, cooled to 0°. The mixture is treated portion-wise with 18.25 g of sodium borohydride, stirred for 1 hour, subsequently poured onto ice and thoroughly extracted with diethyl ether. The ether extract is dried over sodium sulphate and evaporated under reduced pressure. The remaining 2,3,6-trimethylbenzyl alcohol is further processed as follows:

75 g of 2,3,6-trimethylbenzyl alcohol are dissolved in 175 ml of low-boiling petroleum ether. The solution is treated dropwise within 2 hours at −10° C. with a solution of 51 g of phosphorus tribromide in 60 ml of low-boiling petroleum ether. The reaction mixture is stirred for 12 hours at room temperature, then poured onto ice and extracted with diethyl ether. The ether extract is washed first with an ice-cold, saturated, aqueous sodium bicarbonate solution, then with a saturated aqueous common salt solution, dried over sodium sulphate and evaporated under reduced pressure. The remaining 2,3,6-trimethylbenzyl bromide boils, after rectification, at 75°–80° C./0.05 mm Hg.

73.3 g of 2,3,6-trimethylbenzyl bromide are dissolved in 170 ml of benzene. The solution is treated with 90.0 g of triphenyl phosphine. In so doing, the temperature rises to 40° C. The mixture is stirred for 12 hours at room temperature. The precipitated 2,3,6-trimethylbenzyl-triphenylphosphonium bromide melts, after washing with low-boiling petroleum ether and drying, at 240°–242° C.

EXAMPLE 9

After the addition of a slight amount of iron (III) nitrate, 2700 ml of liquid ammonia are treated portionwise with stirring and cooling with 169.5 g of potassium. As soon as the initially blue coloration has disappeared, i.e. after about 30–45 minutes, acetylene gas in a stream of 3 l/min. is led in until the dark coloration of the reaction mixture becomes lighter. Then, the gas stream is reduced to 2 l/min. and the mixture treated dropwise with a solution of 500 g of methylglyoxaldimethylacetal in 425 ml of abs. diethyl ether. The gassing with acetylene is continued for 1 hour with stirring. The reaction mixture is subsequently treated portionwise with 425 g of ammonium chloride, gradually warmed to 30° C. within 12 hours with evaporation of the ammonia and extracted with 1600 ml of diethyl ether. The ether extract is dried over sodium sulphate and evaporated under reduced pressure. The remaining 4,4-dimethoxy-3-methyl-but-1-yn-3-ol boils, after rectification, at 33° C./0.03 mm Hg; $n_D^{25}=1.4480$.

198 g of 4,4-dimethoxy-3-methyl-but-1-yn-3-ol are dissolved in 960 ml of high-boiling petroleum ether and, after the addition of 19.3 5% palladium catalyst and 19.3 g of quinoline, hydrogenated under normal conditions. After the uptake of 33.5 l of hydrogen, the hydrogenation is stopped. The catalyst is filtered off. The filtrate is evaporated under reduced pressure. The remaining 4,4-dimethoxy-3-methyl-but-1-en-3-ol boils, after rectification, at 70°–72° C./18 mm Hg.

195 ml of phosgene are led into 1570 ml of carbon tetrachloride at −10° C. After the addition of 213 g of pyridine, the solution is treated dropwise at a temperature of −10° to −20° C. with 327 4,4-dimethoxy-3-methyl-but-1-en-3-ol. The reaction mixture is slowly warmed to 25° C. with stirring, stirred for a further 3 hours at room temperature, cooled to 15° C. and treated with 895 ml of water. The aqueous phase is separated and rejected. The organic phase is treated, after standing for 12 hours in the cold, with 448 ml of 5% by weight aqueous sulphuric acid, stirred for 5 hours, then washed with water, dried over sodium sulphate and evaporated under reduced pressure. The remaining 2-formyl-4-chloro-but-2-ene boils, after rectification, at 37°–40° C./1.8 mm Hg; $n_D^{25}=1.4895$.

165.7 g of 2-formyl-4-chloro-but-2-ene are dissolved in 840 ml of benzene and treated with 367 g of triphenyl phosphine. The reaction mixture is heated to boiling under reflux conditions for 12 hours with nitrogen gassing, then cooled to 20° C. The precipitated 2-formyl-but-2-ene-4-triphenyl-phosphonium chloride melts, after washing with benzene and drying, at 250°–252° C.

212.6 g of 2-formyl-but-2-ene-4-triphenylphosphonium chloride and 95 g of 3-formylcrotonic acid butyl ester are introduced into 1100 ml of butanol and treated at 5° C. with a solution of 57 g of triethylamine in 60 ml of butanol. The reaction mixture is subsequently stirred for 6 hours at 25° C., then cooled and introduced into water and thoroughly extracted with hexane. The hexane phase is washed first repeatedly with methanol/water (6:4 parts by volume), then with water, dried over sodium sulphate and filtered. The filtrate is isomerised for 12 hours by shaking with iodine. The iodine is removed by the addition of sodium thiosulphate. The filtrate is washed again with water, dried and evaporated under reduced pressure. The remaining 7-formyl-3-methyl-octa-2,4,6-trien-1-oic acid butyl ester boils, after rectification, at 102°–105° C./0.09 mm Hg.

EXAMPLE 10

By the procedure of Example 6:
2,4,6-triisopropyl-benzyl-triphenylphosphonium bromide is condensed with
7-formyl-3-methyl-octa-2,4,6-trien-1-oic acid butyl ester to form
9-(2,4,6-triisopropyl-phenyl)-3,7-dimethyl-nona-2,4,6,8-tetraen-1-oic acid butyl ester (oil);
which is hydrolyzed by the procedure of Example 7 to form:
9-(2,4,6-triisopropyl-phenyl)-3,7-dimethyl-nona-2,4,6,8-tetraen-1-oic acid m.p.: 221° C.

EXAMPLE 11

136 g of 1,3,5-triisopropyl-benzene, 228 ml of acetic acid, 420 ml of conc. hydrochloric acid and 55 g of formaldehyde (35%) are heated to 60° C. The reaction mixture is stirred at this temperature firstly for 3 hours, then, after the renewed addition of 21 g of formaldehyde (35%), for a further 12 hours, then cooled to room temperature and thoroughly extracted with benzene. The benzene extract is washed successively with water, with a saturated aqueous sodium bicarbonate solution and again with water, dried over sodium sulphate and evaporated under reduced pressure. The remaining 2,4,6-triisopropyl-benzyl chloride boils, after rectification, at 70° C./0.05 mm Hg.

69.6 g of 2,4,6-triisopropyl-benzyl chloride are dissolved in 1000 ml of xylene. The solution is treated with 79.5 g of triphenyl phosphine. The mixture is stirred for 18 hours at 125° C., then cooled. The 2,4,6-triisopropyl-benzyl-triphenylphosphonium chloride already precipitated at 80° C. melts, after trituration and washing with benzene, at 237°–238° C.

EXAMPLE 12

By the procedure of Example 6:
pentamethyl-benzyl-triphenylphosphonium chloride is condensed with
7-formyl-3-methyl-octa-2,4,6-trien-1-oic-acid butyl ester to produce
9-(pentamethyl-phenyl)-3,7-dimethyl-nona,2,4,6,8-tetraen-1-oic acid butyl ester (oil);
which is hydrolyzed by the procedure of Example 7 to the 9-(pentamethyl-phenyl)-3,7-dimethyl-nona-2,4,6,8-tetraen-1-oic acid m.p.: 228°–229° C.

EXAMPLE 13

184.5 g of pentamethylbenzene, 193 ml of glacial acetic acid, 355 ml of conc. hydrochloric acid and 44 g of formaldehyde (35%) are heated to 65° C. The reaction mixture is stirred at this temperature first for 3 hours, then, after the renewed addition of 18.1 g of formaldehyde (35%) for a further 3 hours, then cooled to room temperature and thoroughly extracted for a further 12 hours with benzene. The benzene extract is washed successively with water, diluted aqueous sodium hydroxide and water, dried over sodium sulphate and evaporated under reduced pressure. The remaining pentamethyl-benzyl chloride melts, after recrystallisation from hexane, at 80°–81° C.

101.6 g of pentamethyl-benzyl chloride, 149 g of triphenyl phosphine and 250 ml of toluene are stirred for 5 hours at 100° C. The pentamethyl-benzyl-triphenylphosphonium chloride precipitated with cooling of the reaction mixture, melts, after trituration and washing with low-boiling petroleum ether, at 258°–259° C.

EXAMPLE 14

16 g of 3-chloro-2,4,6-trimethyl-benzyl-triphenylphosphonium chloride and 10 g of 7-formyl-3-methyl-octa-2,4,6-trien-1-oic acid butyl ester are heated to boiling with stirring after the addition of 40 g of 1,2-butylene oxide. The 1,2-butylene oxide is slowly distilled off. The reaction mixture is stirred for 30 minutes at 80°–82° C., then cooled and thoroughly extracted with hexane. The hexane extract is shaken out 5 times with 50 ml of methanol/water 70:30 parts by volume each time, then dried over sodium sulphate and evaporated under reduced pressure to produce 9-(3-chloro-2,4,6-trimethylphenyl), 3,7-dimethyl-nona-2,4,6,8-tetraen-1-oic acid butyl ester as a residue.

EXAMPLE 15

5 g of 9-(3-chloro-2,4,6-trimethyl-phenyl)-3,7-dimethyl-nona-2,4,6,8-tetraen-1-oic acid butyl ester are heated to boiling under nitrogen gassing in 50 ml of a 5% by weight ethanolic potassium hydroxide solution. The solution becoming clear with boiling is cooled after 30 minutes, introduced into water and made acidic by the addition of the acetic acid. The precipitated 9-(3-chloro-2,4,6-trimethyl-phenyl)-3,7-dimethyl-nona-2,4,6,8-tetraen-1-oic acid melts, after recrystallisation from benzene, at 208°–209° C.

EXAMPLE 16

119 g of chloromesitylene, 11.9 g of paraformaldehyde and 5.95 g of zinc chloride (anhydrous) are heated to 60° C. and gassed with hydrogen chloride, with stirring, firstly for 8 hours and, after the addition of a further 11.9 g of paraformaldehyde, for a further 8 hours. The reaction mixture is then poured onto ice and thoroughly extracted with diethyl ether. The ether extract is washed successively with water, with a saturated aqueous sodium bicarbonate solution and with water, dried over sodium sulphate and evaporated. The remaining 3-chloro-2,4,6-trimethyl-benzyl chloride boils, after rectification, at 138° C./17 mm Hg.

71.25 g of 3-chloro-2,4,6-trimethyl-benzyl chloride, 92 g of triphenyl phosphine and 375 ml of abs. toluene are heated at 100° C. for 12 hours. The 3-chloro-2,4,6-trimethyl-benzyl-triphenylphosphonium chloride precipitated with cooling melts at 233°–235° C.

EXAMPLE 17

By the procedure given in Example 14

3-nitro-2,4,6-trimethyl-benzyl-triphenylphosphonium chloride is condensed with
7-formyl-3-methyl-hepta-2,4,6-trien-1-oic acid butyl ester to form
9-(3-nitro-2,4,6-trimethyl-phenyl)-3,7-dimethyl-nona-2,4,6,8-tetraen-1-oic acid butyl ester (oil); which is converted by the procedure of Example 15 to:
9-(3-nitro-2,4,6-trimethyl-phenyl)-3,7-dimethyl-nona-2,4,6,8-tetraen-1-oic acid, m.p. 205°–206° C.

EXAMPLE 18

10 g of nitromesitylene, 2 g of p-formaldehyde and 1 g of zinc chloride (anhydrous) are heated to 60° C. and gassed with hydrogen chloride for 16 hours with stirring. The reaction mixture is then poured onto ice and thoroughly extracted with diethyl ether. The ether extract is washed successively with water, a saturated, aqueous sodium bicarbonate solution and with water, dried over sodium sulphate and evaporated. The remaining 3-nitro-2,4,6-trimethyl-benzyl chloride, an oil, $n_D^{22}=1.5373$, is further processed as follows.

11.6 g of 3-nitro-2,4,6-triphenyl-benzyl chloride, 14 g of triphenyl phosphine and 100 ml of abs. benzene are heated to boiling under reflux conditions for 24 hours. The 3-nitro-2,4,6-trimethyl-benzyl-triphenylphosphonium chloride precipitated with cooling melts at 252°–253° C.

EXAMPLE 19

By the procedure of Example 14:
4-methoxy-2,3,5,6-tetramethyl-benzyl-triphenylphosphonium chloride is condensed with
7-formyl-3-methyl-octa-2,4,6-trien-1-oic acid butyl ester to form:
9-(4-methoxy-2,3,5,6-tetramethyl-phenyl)-3,7-dimethyl-nona-2,4,6,8-tetraen-1-oic acid butyl ester (oil); which is converted by the procedure of Example 15 to:
9-(4-methoxy-2,3,5,6-tetramethyl-phenyl)-3,7-dimethyl-nona-2,4,6,8-tetraen-1-oic acid, m.p. 230°–233° C.

EXAMPLE 20

15 g of 2,3,5,6-tetramethylphenol are dissolved in 55.3 ml of methanol and, after the addition of 7.25 g of potassium hydroxide in 5.5 ml of water, treated dropwise at 0°–5° C. with 18.8 g of methyl iodide. The reaction mixture is stirred for 2 hours at room temperature and subsequently for 12 hours at 60° C., then cooled, diluted with 150 ml of water and extracted with 100 ml of diethyl ether. The ether extract is washed successively with 3N sodium hydroxide and water, dried over sodium sulphate and evaporated under reduced pressure. The remaining 2,3,5,7-tetramethylanisole melts, after purification by absorption on silica gel (eluent: methylene chloride), at 53°–55° C.

43 g of 2,3,5,6-tetramethylanisole in 110 ml of acetic acid anhydrous are introduced into 203 ml of 37% by weight aqueous hydrochloric acid and treated dropwise with 21.6 g of 37% formaldehyde. The reaction mixture is heated to 70° C. for 3 hours with stirring and, after the renewed addition of 8.3 g of 37% formaldehyde, stirred for a further 3 hours at 70° C. The mixture is subsequently cooled to room temperature and extracted with 500 ml of benzene. The benzene extract is separated. The aqueous phase is shaken out with benzene. The combined benzene extracts are washed successively with water, with a saturated, aqueous sodium carbonate solution and again with water, dried and evaporated under reduced pressure. The remaining 4-methoxy-2,3,5,6-tetramethyl-benzyl chloride melts, after recrystallisation from ethyl acetate/hexane (1:3 parts by volume) at 104°–105° C.

28 g of 4-methoxy-2,3,5,6-tetramethyl-benzyl chloride, 34.7 g of triphenyl phosphine and 153 ml of toluene are heated at 100° C. for 12 hours. The 4-methoxy-2,3,5,6-tetramethyl-benzyl-triphenylphosphonium chloride precipitated with cooling melts at 251°–252° C.

EXAMPLE 21

60 g of 9-(4-methoxy-2,3,6-trimethyl-phenyl)-3,7-dimethyl-nona-2,4,6,8-tetraen-1-oic acid are dissolved in 1000 ml of acetone. After the addition of 128 g of methyl iodide and 128 g of potassium carbonate, the solution is stirred under nitrogen gassing for 16 hours at 55°–60° C. and subsequently evaporated under reduced pressure. The residue is dissolved in 1300 ml of petroleum ether (boiling point 80°–105° C.). The 9-(4-methoxy-2,3,6-trimethyl-phenyl)-3,7-dimethyl-nona-2,4,6,8-tetraen-1-oic acid methyl ester crystallising out at −20° C., melts at 98°–99° C.

EXAMPLE 22

By the procedure of Example 21:
9-(4-methoxy-2,3,6-trimethyl-phenyl)-3,7-dimethyl-nona-2,4,6,8-tetraen-1-oic acid and ethyl iodide is converted to
9-(4-methoxy-2,3,6-trimethyl-phenyl)-3,7-dimethyl-nona-2,4,6,8-tetraen-1-oic acid ethyl ester; m.p.: 104°–105° C.;
9-(4-methoxy-2,3,6-trimethyl-phenyl)-3,7-dimethyl-nona-2,4,6,8-tetraen-1-oic acid and isopropyl iodide is converted to
9-(4-methoxy-2,3,6-trimethyl-phenyl)-3,7-dimethyl-nona-2,4,6,8-tetraen-1-oic acid isopropyl ester; (oil).

EXAMPLE 23

28.6 g of 9-(4-methoxy-2,3,6-trimethyl-phenyl)-3,7-dimethyl-nona-2,4,6,8-tetraen-1-oic acid are introduced into 300 ml of benzene and treated under nitrogen gassing with 12 g of phosphorus trichloride. The benzene is subsequently distilled off under reduced pressure. The remaining 9-(4-methoxy-2,4,6-trimethyl-phenyl)-3,7-dimethyl-nona,2,4,6,8-tetraen-1-oic acid chloride is dissolved in 1200 ml of diethyl ether. The solution is added dropwise at −33° C. into 500 ml of liquid ammonia and stirred for 3 hours. The reaction mixture is then diluted with 500 ml of diethyl ether and stirred without cooling for a further 12 hours, the ammonia evaporating. The residue is dissolved in 10 l of methylene chloride. The solution is washed 2 times with 3 l of water, dried over sodium sulphate and evaporated under reduced pressure. The remaining 9-(4-methoxy-2,3,6-trimethyl-phenyl)-3,7-dimethyl-nona-2,4,6,8-tetraen-1-oic acid amide melts, after recrystallisation from ethanol, at 207°–209° C.

EXAMPLE 24

By the procedure of Example 23:
9-(4-methoxy-2,3,6-trimethyl-phenyl)-3,7-dimethyl-nona-2,4,6,8-tetraen-1-oic acid chloride and ethylamine are converted to
9-(4-methoxy-2,3,6-trimethyl-phenyl)-3,7-dimethyl-nona-2,4,6,8-tetraen-1-oic acid ethyl amide; m.p. 179°–180° C.; and 9-(4-methoxy-2,3,6-trimethyl-phenyl)-3,7-dimethyl-nona-2,4,6,8-tetraen-1-oic acid chloride and diethylamine are converted to
9-(4-methoxy-2,3,6-trimethyl-phenyl)-3,7-dimethyl-nona-2,4,6,8-tetraen-1-oic acid diethyl amide; m.p. 105°–106° C.

EXAMPLE 25

Manufacture of a capsule filling material of the following composition:

| | |
|---|---|
| 9-(4-Methoxy-2,3,6-trimethyl-phenyl)-3,7-dimethyl-nona-2,4,6,8-tetraen-1-oic acid ethyl ester | 0.1 g |
| Wax mixture | 51.4 g |
| Vegetable Oil | 103.0 g |
| Trisodium salt of ethylenediamine tetraacetic acid | 0.5 g |
| Individual weight of a capsule | 150 mg |
| Active material content of a capsule | 10 mg |

EXAMPLE 26

Manufacture of an ointment containing 0.3% active material of the following composition:

| | |
|---|---|
| 9-(4-Methoxy-2,3,6-trimethyl-phenyl)-3,7-dimethyl-nona-2,4,6,8-tetraen-1-oic acid | 0.3 g |
| Cetyl alcohol | 2.7 g |
| Lanoline | 6.0 g |
| White Vaseline | 15.0 g |
| Dist. water q.s. ad | 100.0 g |

EXAMPLE 27

Manufacture of a water/fat emulsion containing 0.3% active material of the following composition:

| | |
|---|---|
| 9-(4-Methoxy-2,3,6-trimethyl-phenyl)-3,7-dimethyl-nona-2,4,6,8-tetraen-1-oic acid ethyl amide | 0.3 g |
| Magnesium stearate | 2.0 g |
| Perhydrosqualene | 13.0 g |

EXAMPLE 28

Manufacture of a solution containing 0.1% active material of the following composition:

| | |
|---|---|
| 9-(4-Methoxy-2,3,6-trimethyl-phenyl)-3,7-trimethyl-nona-2,4,6,8-tetraen-1-oic acid | 0.1 g |
| Dimethyl sulphoxide | 70.0 g |
| Water q.s. ad | 100 ml |

EXAMPLE 29

By the procedure of Example 1 9-(4-allyloxy-2,3,6-trimethyl-phenyl)-3,7-dimethyl-nona-2,4,6,8-tetraen-1-oic acid ethyl ester is manufactured from 5-(4-allyloxy-2,3,6-trimethyl-phenyl)-3-methyl-penta-2,4-diene-1-triphenylphosphonium bromide by reaction with 3-formyl-crotonic acid ethyl ester. This product is converted to 9-(4-allyloxy-2,3,6-trimethyl-phenyl)-3,7-dimethyl-nona-2,4,6,8-tetraen-1-oic acid of melting point 198°–200° C. by the procedure of Example 2.

The 5-(4-allyloxy-2,3,6-trimethyl-phenyl)-3-methyl-penta-2,4-diene-1-triphenylphosphonium bromide employed as the starting material can be prepared by the procedure of Example 3. This procedure is carried out by alkylation of 1,3,5-trimethylphenol with allyl bromide to give 1,3,5-trimethyl-phenyl allyl ether (boiling point 76°–80° C./0.05 mmHg), by formylation of the ether obtained to give 4-allyloxy-2,3,6-trimethyl-benzaldehyde (boiling point 90°–102° C./0.15 mmHg), by condensation of the aldehyde obtained with acetone to give 4-(4-allyloxy-2,3,6-trimethyl-phenyl)-but-3-en-1-al (boiling point 135°–138° C./0.05 mmHg), by reaction of the ketone obtained with acetylene to give 5-(4-allyloxy-2,3,6-trimethyl-phenyl)-3-methyl-3-hydroxy-penta-4-en-1-yne, by partial hydrogenation of the tertiary acetylene carbinol obtained to give 5-(4-allyloxy-2,3,6-trimethyl-phenyl)-3-methyl-3-hydroxy-penta-1,4-diene and by reaction of the tertiary ethylene carbinol obtained with triphenylphosphine hydrobromide. There is obtained 5-(4-allyloxy-2,3,6-trimethyl-phenyl)-3-methyl-penta-2,4-diene-triphenylphosphonium bromide which melts at 114°–116° C.

EXAMPLE 30

By the procedure of Example 14, 9-(2,4,6-trimethyl-phenyl)-3,7-dimethyl-nona-2,4,6,8-tetraen-1-oic acid butyl ester is manufactured from 2,4,6-trimethyl-benzyl-triphenylphosphonium chloride by reaction with 7-formyl-3-methyl-octa-2,4,6-trien-1-oic acid butyl ester. This product is converted to 9-(2,4,6-trimethyl-phenyl)-3,7-dimethyl-nona-2,4,6,8-tetraen-1-oic acid of melting point 214°–215° C. by the procedure of Example 15.

The 2,4,6-trimethyl-benzyl-triphenylphosphonium chloride employed as the starting material is prepared by the procedure described in Example 18 by haloformylation of mesitylene to give 2,4,6-trimethyl-benzyl chloride (boiling point 112° C./12 mm Hg) and reaction of the latter compound with triphenylphosphine.

EXAMPLE 31

By the procedure of Example 14, 9-(2,3,4,6-tetramethyl-phenyl)-3,7-dimethyl-nona-2,4,6,8-tetraen-1-oic acid butyl ester is manufactured from 2,3,4,6-tetramethyl-benzyltriphenylphosphonium chloride by reaction with 7-formyl-3-methyl-octa-2,4,6-trien-1-oic acid butyl ester. From this product, there is produced by the procedure of Example 15 9-(2,3,4,6-tetra-methyl-phenyl)-3,7-dimethyl-nona-2,4,6,8-tetraen-1-oic acid of melting point 201°–202° C.

The 2,3,4,6-tetramethyl-benzyl-triphenylphosphonium chloride employed as the starting material is prepared by the procedure described in Example 16 by haloformylation of 1,2,3,5-tetramethyl-benzene to give 2,3,4,6-tetramethylbenzyl chloride ($n_D^{20}=1.5571$) and reaction of the latter compound with triphenylphosphine.

EXAMPLE 32

By the procedure described in Example 14, 9-(4-methoxy-2,6-dimethyl-phenyl)-3,7-dimethyl-nona-2,4,6,8-tetraen-1-oic acid butyl ester is manufactured from 4-methoxy-2,6-dimethylbenzyl-triphenylphosphonium chloride by reaction with 7-formyl-3-methyl-octa-2,4,6-trien-1-oic acid butyl ester. From this product, there is produced by the procedure of Example 15, 9-(4-methoxy-2,6-dimethyl-phenyl)-3,7-dimethyl-nona-2,4,6,8-tetraen-1-oic acid of melting point 207°–208° C.

The 4-methoxy-2,6-dimethyl-benzyl-triphenylphosphonium chloride employed as the starting material is prepared by the procedure described in Example 16 by haloformylation of 3,5-dimethylanisole to give 4-methoxy-2,6-dimethyl-benzyl chloride ($n_D^{20}=1.5475$) and reaction of the latter compound with triphenylphosphine.

EXAMPLE 33

By the procedure described in Example 14, 9-(3-methoxy-2,4,6-trimethyl-phenyl)-3,7-dimethyl-nona-2,4,6,8-tetraen-1-oic acid butyl ester is manufactured from 3-methoxy-2,4,6-trimethyl-benzyl-triphenylphosphonium chloride by reaction with 7-formyl-3-methyl-octa-2,4,6-trien-1-oic acid butyl ester. This product is converted to 9-(3-methoxy-2,4,6-trimethylphenyl)-3,7-dimethyl-nona-2,4,6,8-tetraen-1-oic acid of melting point 196°–198° C., utilizing the procedure described in Example 15.

The 3-methoxy-2,4,6-trimethyl-benzyl-triphenylphosphonium chloride employed as the starting material is prepared by the procedure described in Example 16 by haloformylation of 2,4,6-trimethylanisole to give 3-methoxy-2,4,6-trimethyl-benzyl chloride ($n_D^{27}=1.5415$) and reaction of the latter compound with triphenylphosphine. The 3-methoxy-2,4,6-trimethyl-benzyl-triphenylphosphonium chloride melts at 308°–310° C.

EXAMPLE 34

By the procedure described in Example 14, 9-(4-methoxy-3-allyl-2,6-dimethyl-phenyl)-3,7-dimethyl-nona-2,4,6,8-tetraen-1-oic acid butyl ester is manufactured from 4-methoxy-3-allyl-2,6-dimethyl-benzyl-triphenylphosphonium chloride by reaction with 7-formyl-3-methyl-octa-2,4,6-trien-1-oic acid butyl ester. This product is converted by the procedure of Example 15 to 9-(4-methoxy-3-allyl-2,6-dimethyl-phenyl)-3,7-dimethyl-nona-2,4,6,8-tetraen-1-oic acid of melting point 160° C.–161° C.

The 4-methoxy-3-allyl-2,6-dimethyl-benzyl-triphenylphosphonium chloride employed as the starting material is prepared by the procedure described in Example 16 by haloformylation of 3,5-dimethyl-2-allyl-anisole to give 4-methoxy-3-allyl-2,6-dimethyl-benzyl chloride ($n_D^{20}=1.5690$) and reaction of the latter compound with triphenylphosphine.

EXAMPLE 35

By the procedure described in Example 14, 9-(4-methoxy-3-nitro-2,6-dimethyl-phenyl)-3,7-dimethyl-nona-2,4,6,8-tetraen-1-oic acid ethyl ester is manufactured from 4-methoxy-3-nitro-2,6-dimethyl-benzyl-triphenylphosphonium chloride by reaction with 7-formyl-3-methyl-octa-2,4,6-trien-1-oic acid ethyl ester. This product is converted by the procedure of Example 15 to 9-(4-methoxy-3-nitro-2,6-dimethyl-phenyl)-3,7-dimethyl-nona-2,4,6,8-tetraen-1-oic acid of melting point 109°–110° C.

The 4-methoxy-3-nitro-2,6-dimethyl-benzyl-triphenylphosphonium chloride employed as the starting material is prepared by the procedure described in Example 16 by haloformylation of 2-nitro-3,5-dimethylanisole to give 4-methoxy-3-nitro-2,6-dimethyl-benzyl chloride (melting point 109°–110° C.) and reaction of the latter compound with triphenylphosphine. The 4-methoxy-3-nitro-2,6-dimethyl-benzyl-triphenylphosphonium chloride melts at 230°–232° C.

EXAMPLE 36

By the procedure described in Example 14, 9-(4-ethoxy-2,3,6-trimethyl-phenyl)-3,7-dimethyl-nona-2,4,6,8-tetraen-1-oic acid ethyl ester (melting point 96°–97° C.) is manufactured from 4-ethoxy-2,3,6-trimethyl-benzyl-triphenylphosphonium chloride by reaction with 7-formyl-3-methyl-octa-2,4,6-trien-1-oic acid ethyl ester.

The 4-ethoxy-2,3,6-trimethyl-benzyl-triphenylphosphonium chloride employed as the starting material is prepared by the procedure described in Example 18 by alkylation of 2,3,5-trimethylphenol to give 2,3,5-trimethyl-phenyl ethyl ether (melting point 93°–95° C.), by haloformylation of the ether obtained to give 4-ethoxy-2,3,6-trimethyl-benzyl chloride (melting point 63°–64° C.) and by reaction of the latter compound with triphenylphosphine.

EXAMPLE 37

By the procedure described in Example 14, 9-(4-isopropoxy-2,3,6-trimethyl-phenyl)-3,7-dimethyl-nona-2,4,6,8-tetraen-1-oic acid butyl ester is manufactured from 4-isopropoxy-2,3,6-trimethyl-benzyl-triphenylphosphonium chloride by reaction with 7-formyl-3-methyl-octa-2,4,6-trien-1-oic acid butyl ester. This product, is converted by the procedure of Example 15 to 9-(4-isopropoxy-2,3,6-trimethylphenyl)-3,7-dimethyl-nona-2,4,6,8-tetraen-1-oic acid of melting point 176°–177° C.

The 4-isopropoxy-2,3,6-trimethyl-benzyl-triphenylphosphonium chloride employed as the starting material is prepared by the procedure described in Example 18 by alkylation of 2,3,5-trimethylphenol to give 2,3,5-trimethylphenyl isopropyl ether (boiling point 115° C./11 mmHg), by haloformylation of the ether obtained to give 4-isopropoxy-2,3,6-trimethyl-benzyl chloride ($n_D^{20}$=1.5433) and by reaction of the latter compound with triphenylphosphine.

EXAMPLE 38

By the procedure described in Example 14, 9-(3-dimethylamino-2,4,6-trimethyl-phenyl)-3,7-dimethyl-nona-2,4,6,8-tetraen-1-oic acid ethyl ester (bright-yellow oil) is manufactured from 3-dimethylamino-2,4,6-trimethyl-benzyl-triphenylphosphonium chloride by reaction with 7-formyl-3-methyl-octa-2,4,6-trien-1-oic acid ethyl ester.

The 3-dimethylamino-2,4,6-trimethyl-benzyl-triphenylphosphonium chloride employed as the starting material is prepared by the procedure described in Example 16 by haloformylation of N,N-dimethylmesidine to give 3-dimethylamino-2,4,6-trimethyl-benzyl chloride (boiling point 71° C./11 mmHg) and reaction of the latter compound with triphenylphosphine.

EXAMPLE 39

1.7 g of 8-diethoxy-phosphono-3,7-dimethyl-octa-2,4,6-trien-1-oic acid ethyl ester are introduced in 8.0 ml of tetrahydrofuran. The solution is cooled to 0° C. after addition of 0.27 g of sodiumhydride (50–60%), then stirred 30 minutes at 0° C. and thereafter a solution of 0.96 g of 2,3,6-trimethyl-p-anisaldehyde in 3 ml of tetrahydrofuran is added dropwise during 15 minutes. The reaction mixture is stirred 7 hours at room temperature, then poured into ice and, after addition of 2N hydrochloric acid, extracted with diethyl ether. The ether extract is washed neutral with water, dried over sodium sulfate and evaporated under reduced pressure. The remaining 9-(4-methoxy-2,3,6-trimethyl-phenyl)-3,7-dimethyl-nona-2,4,6,8-tetraen-1-oic acid ethyl ester melts at 104°–105° C.

Instead of sodium hydride (0.27 g), employed above, an alkali metal alcoholate can also be used as condensation agent, e.g. sodium ethylate (0.125 g of sodium in 5 ml ethanol).

EXAMPLE 40

3.03 g of 8-bromo-3,7-dimethyl-octa-2,4,6-trien-1-oic acid ethyl ester are heated with 1.66 g of triethylphosphite slowly to 125° C. The surplus bromo ester is distilled off. The residue is cooled and poured into ice and extracted with diethyl ether and an aqueous solution of sodium-hydrogen carbonate, dried and evaporated under reduced pressure. The remaining 8-diethoxy-phosphono-3,7-dimethyl-octa-2,4,6-trien-1-oic acid ethyl ester is immediately treated, as described above, with 2,3,6-trimethyl-p-anisaldehyde.

EXAMPLE 41

2 g of 1-(phenyl-sulfonyl)-methyl-4-methoxy-2,3,6-trimethyl-benzene are introduced in 10 ml of tetrahydrofuran. The solution is cooled to −78° C. and, after the addition of 0.51 g of butyl lithium, treated with a solution of 1.8 g 8-bromo-3,7-dimethyl-octa-2,4,6-trien-1-oic acid ethyl ester in 8 ml of tetrahydrofuran. The reaction mixture is stirred 2 hours at −78° C., 2 hours at −40° C. and 16 hours at 0° to +5° C. The mixture is poured into ice and, after addition of 2N hydrochloric acid, extracted with diethyl ether. The ether extract is washed neutral with water, dried over sodium sulfate and evaporated under reduced pressure. The remaining 9-(4-methoxy-2,3,6-trimethyl-phenyl)-9-(phenyl-sulfonyl)-3,7-dimethyl-nona-2,4,6-trien-1-oic acid ethyl ester (2.8 g) is diluted with 8 ml of abs. ethanol. The solution is treated at 0° C. in 2 portions with 1.2 g of sodium ethylate powder. The mixture is stirred 30 minutes at 0° C., then 2 hours at 80° C., thereafter cooled, poured into ice and, after the addition of 2N hydrochloric acid, extracted with diethyl ether. The ether extract is washed neutral with water, dried over sodium sulfate and evaporated under reduced pressure. The remaining 9-(4-methoxy-2,3,6-trimethyl-phenyl)-3,7-dimethyl-nona-2,4,6,8-tetraen-1-oic acid ethyl ester melts at 105° to 105° C.

EXAMPLE 42

16.8 g of 4-methoxy-2,3,6-trimethyl-benzyl alcohol, 17.4 g of sodium salt of benzene sulfinic acid, 20.0 ml of isopropanol and 30.0 ml of glacial acetic acid are heated 16 hours under nitrogen and reflux conditions. The reaction mixture is cooled, treated portionwise with 200 ml of water and neutralized by the addition of sodium hydrogen carbonate. The organic layer is separated, washed several times with an aqueous solution of sodium-hydrogen-carbonate (5% by weight), dried over sodium sulfate and evaporated under reduced pressure. The remaining 1-(phenyl-sulfonyl)-methyl-4-methoxy-2,3,6-trimethyl-benzene shows the following I.R.: 1592, 1580, 1302, 1149, 118 cm$^{-1}$.

EXAMPLE 43

1.08 g of 4-methoxy-2,3,6-trimethyl-benzylchloride, 1.67 g of 8-(phenyl-sulfonyl)-3,7-dimethyl-octa-2,4,6-trien-1-oic acid ethyl ester and 10 ml of dimethyl formamide are cooled to 0° C. and treated with 0.374 of solid sodium ethanolate. The reaction mixture is stirred 30 minutes at room temperature, then poured into ice and, after the addition of 2N hydrochloric acid, extracted with diethyl ether. The ether extracted is washed neutral, dried over sodium sulfate and evaporated under reduced pressure. The remaining 9-(4-methoxy-2,3,6-trimethyl-phenyl)-8-(phenyl-sulfonyl)-3,7-dimethyl-nona-2,4,6,8-trien-1-oic acid ethyl ester is (as described in Example 42) with the formation of benzene sulfonic acid as side product and additional carbon-carbon double bond in the main product, transformed into the desired 9-(4-methoxy-2,3,6-trimethyl-phenyl)-3,7-dimethyl-nona-2,4,6,8-tetraen-1-oic acid ethyl ester (m.p. 104°–105° C.).

EXAMPLE 44

8.5 g of 8-bromo-3,7-dimethyl-octa-2,4,6-trien-1-oic acid ethyl ester are dissolved into 95 ml of dimethyl sulfoxide. The solution is treated under nitrogen in the cold with 0.45 g of sodium salt of benzene sulfinic acid. The mixture is stirred 1 hour at room temperature, then poured into ice and extracted with diethyl ether. The ether extract is washed with water, dried over sodium sulfate and evaporated under reduced pressure. The remaining 8-(phenyl-sulfonyl)-3,7-dimethyl-octa-2,4,6-trien-1-oic acid ethyl ester melts at 114°–115° C.

EXAMPLE 45

By the procedure of Example 21:
9-(4-methoxy-2,3,5,6-tetramethyl-phenyl)-3,7-dimethyl-nona-2,4,6,8-tetraen-1-oic acid ethyl ester (melting point 105°–106° C.) is manufactured from 9-(4-methoxy-2,3,5,6-tetramethyl-phenyl)-3,7-dimethyl-nona-2,4,6,8-tetraen-1-oic acid and ethyl iodide;
9-(4-methoxy-2,3,6-trimethyl-phenyl)-3,7-dimethyl-nona-2,4,6,8-tetraen-1-oic acid 2-diethylaminoethyl ester (bright-yellow oil) is manufactured from 9-(4-methoxy-2,3,6-trimethyl-phenyl)-3,7-dimethyl-nona-2,4,6,8-tetraen-1-oic acid and diethylaminoethyl chloride;
and 9-(4-methoxy-2,3,6-trimethyl-phenyl)-3,7-dimethyl-nona-2,4,6,8-tetraen-1-oic acid (3-pyridyl) methyl ester (melting point 113°–114° C.) is manufactured from 9-(4-methoxy-2,3,6-trimethyl-phenyl)-3,7-dimethyl-nona-2,4,6,8-tetraen-1-oic acid and beta-picoline chloride.

EXAMPLE 46

20 g of 9-(4-methoxy-2,3,6-trimethyl-phenyl)-3,7-dimethyl-nona-2,4,6,8-tetraen-1-oic acid are dissolved in 200 ml of tetrahydrofuran. After the addition of 5.5 ml of phosphorus trichloride, the solution is stirred for 2 hours at room temperature, cooled to 0° C. and treated firstly with 50 ml of pyridine and then dropwise at 0°–5° C. with 50 ml of propargyl alcohol. The mixture is stirred for 2 hours at room temperature and then diluted with water. The organic phase is washed successively with water, dilute hydrochloric acid and a 2% aqueous sodium bicarbonate solution, dried over sodium sulphate and evaporated. There is obtained 9-(4-methoxy-2,3,6-trimethyl-phenyl)-3,7-dimethyl-nona-2,4,6,8-tetraen-1-oic acid propargyl ester which melts at 94°–95° C. after absorption on aluminium oxide using benzene as the eluent.

EXAMPLE 47

By the procedure of Example 46:
9-(4-methoxy-2,3,6-trimethyl-phenyl)-3,7-dimethyl-nona-2,4,6,8-tetraen-1-oic acid allyl ester (melting point 66°–68° C.) is manufactured from 9-(4-methoxy-2,3,6-trimethyl-phenyl)-3,7-dimethyl-nona-2,4,6,8-tetraen-1-oic acid and allyl alcohol.

EXAMPLE 48

By the procedure of Example 23:
9-(4-methoxy-2,3,5,6-tetramethyl-phenyl)-3,7-dimethyl-nona-2,4,6,8-tetraen-1-oic acid ethylamide (melting point 200°–201° C.) is manufactured from 9-(4-methoxy-2,3,5,6-tetramethyl-phenyl)-3,7-dimethyl-nona-2,4,6,8-tetraen-1-oic acid chloride and ethylamine; and 9-(4-methoxy-2,3,6-trimethyl-phenyl)-3,7-dimethyl-nona-2,4,6,8-tetraen-1-oic acid morpholide is manufactured from 9-(4-methoxy-2,3,6-trimethyl-phenyl)-3,7-dimethyl-nona-2,4,6,8-tetraen-1-oic acid chloride and morpholine.

EXAMPLE 49

15 g of 9-(4-methoxy-2,3,6-trimethyl-phenyl)-3,7-dimethyl-nona-2,4,6,8-tetraen-1-oic acid ethyl ester (50:50 cis/trans mixture) are chromatographed on 1.5 kg of aluminium oxide (activity stage 1) using hexane/diethyl ether (80:20 parts by volume) as the eluent. From the front, there is isolated 9-(4-methoxy-2,3,6-trimethyl-phenyl)-3,7-dimethyl-nona-2-trans,4-cis,6-trans,8-trans-tetraen-1-oic acid ethyl ester as a light-yellow oil.

EXAMPLE 50

The 4-methoxy-2,3,5-trimethyl-benzyl-triphenyl-phosphonium chloride employed as the starting material in Example 51 is prepared in a manner analogous to that described in the aforegoing Example 8, e.g., by the following sequence:
2,3,6-trimethylphenol
2,3,6-trimethylanisole
4-methoxy-2,3,5-trimethyl-benzyl chloride.

EXAMPLE 51

In analogy to the procedure given in Example 6:
4-methoxy-2,6-dimethyl-3-ethyl-benzyl-triphenyl-phosphonium chloride is condensed with 7-formyl-3-methyl-octa-2,4,6-trien-1-oic acid ethyl ester to produce 9-(4-methoxy-2,6-dimethyl-3-ethyl-phenyl)-3,7-dimethyl-nona-2,4,6,8-tetraen-1-oic acid ethyl ester which is converted by the procedure of Example 7 to form 9-(4-methoxy-2,6-dimethyl-3-ethyl-phenyl)-3,7-dimethyl-nona-2,4,6,8-tetraen-1-oic acid, m.p.: 197°–198° C.

EXAMPLE 52

The 4-methoxy-2,6-dimethyl-3-ethyl-benzyl-triphenylphosphonium chloride employed as the starting material in Example 53 can be prepared in a manner analogous to that described in Example 8 by the following sequence:
3,5-dimethylphenol
1-acetoxy-3,5-dimethyl-benzene
2-acetyl-3,5-dimethyl-phenol
2-ethyl-3,5-dimethyl-phenol
2-ethyl-3,5-dimethyl-anisole
4-methoxy-2,6-dimethyl-3-ethyl-benzyl chloride.

EXAMPLE 53

In analogy to the procedure given in Example 6:
4-methoxy-3,5-diethyl-2,6-dimethyl-benzyl-triphenylphosphonium chloride is condensed with 7-formyl-3-methyl-octa-2,4,6-trien-1-oic acid ethyl ester to produce the 9-(4-methoxy-3,5-diethyl-2,6-dimethyl-phenyl)-3,7-dimethyl-nona-2,4,6,8-tetraen-1-oic acid ethyl ester which is converted by the procedure of Example 7 to 9-(4-methoxy-3,5-diethyl-2,6-dimethyl-phenyl)acid, m.p: 153°–154° C.

EXAMPLE 54

The 4-methoxy-3,5-diethyl-2,6-dimethyl-benzyl-triphenylphosphonium chloride employed as starting materials in Example 55 can be prepared in a manner analogous to that described in Example 8 by the following sequence:
3,5-dimethyl-phenol
1-acetoxy-3,5-dimethyl-benzene
2-acetyl-3,5-dimethyl-phenol
2-ethyl-3,5-dimethyl-phenol
1-acetoxy-2-ethyl-3,5-dimethyl-benzene
6-acetyl-2-ethyl-3,5-dimethyl-phenol
2,6-diethyl-3,5-dimethyl-phenol
2,6-diethyl-3,5-dimethyl-anisole
4-methoxy-3,5-diethyl-2,6-dimethyl-benzyl chloride.

EXAMPLE 55

In analogy to the procedure given in Example 6:
4-propoxy-2,3,6-trimethyl-benzyl-triphenyl-phosphonium chloride is condensed with 7-formyl-3-methyl-octa-2,4,6-trien-1-oic acid ethyl ester to produce 9-(4-propoxy-2,3,6-trimethyl-phenyl)-3,7-dimethyl-nona-2,4,6,8-tetraen-1-oic acid ethyl ester which is converted by the procedure of Example 7 to 9-(4-propoxy-2,3,6-trimethyl-phenyl)-3,7-dimethyl-nona-2,4,6,8-tetraen-1-oic acid, m.p.: 200°–201° C.

EXAMPLE 56

The 4-propoxy-2,3,6-trimethyl-benzyl-triphenylphosphonium chloride employed as starting material, can be prepared in a manner analogous to that described in Example 8, e.g., by the following sequence:
2,3,5-trimethylphenol
2,3,5-trimethyl-propoxy-benzene
4-propoxy-2,3,6-trimethyl-benzyl chloride.

EXAMPLE 57

In analogy to the procedure given in Example 6:
4-ethoxy-2,3,6-trimethyl-benzyl-triphenyl-phosphonium chloride is condensed with 7-formyl-3-methyl-octa-2,4,6-trien-1-oic acid ethyl ester to produce 9-(4-ethoxy-2,3,6-trimethyl-phenyl)-3,7-dimethyl-nona-2,4,6,8-tetranoic acid ethyl ester which is converted by the procedure of Example 7 to 9-(4-ethoxy-2,3,6-trimethyl-phenyl)-3,7-dimethyl-nona-2,4,6,8-tetraen-1-oic acid, m.p. 219°–220° C.

EXAMPLE 58

By the procedure of Example 6:
3,5-dichloro-2,4,6-trimethyl-benzyl-triphenyl-phosphonium chloride is condensed with 7-formyl-3-methyl-octa-2,4,6-trien-1-oic acid ethyl ester to form 9-(3,5-dichloro-2,4,6-trimethyl-phenyl)-3,7-dimethyl-nona-2,4,6,8-tetraen-1-oic acid ethyl ester which is converted by the procedure of Example 7 to 9-(3,5-dichloro-2,4,6-trimethyl-phenyl)-3,7-dimethyl-nona-2,4,6,8-tetraen-1-oic acid, m.p: 220°–222° C.

EXAMPLE 59

In analogy to the procedure given in Example 6:
3-chloro-2,4,6-trimethyl-benzyl-triphenyl-phosphonium chloride is condensed with 7-formyl-3-methyl-octa-2,4,6-trien-1-oic acid ethyl ester to produce 9-(3-chloro-2,4,6-trimethyl-phenyl)-3,7-dimethyl-nona-2,4,6,8-tetraen-1-oic acid ethyl ester, m.p.: 84°–85° C.

EXAMPLE 60

The 3-chloro-2,4,6-trimethyl-benzyl-triphenylphosphonium chloride employed as starting material, can be prepared in a manner analogous to that described in the aforegoing Example 8, e.g., by the following sequence:
2,4,6-trimethyl-aniline
2,4,6-trimethyl-chlorobenzene
3-chloro-2,4,6-trimethyl-benzyl chloride.

EXAMPLE 61

36.5 g. of 1-ethoxycarbonyl-2,6-dimethyl-hepta-1,3,5-trien-7-triphenylphosphonium bromide are dissolved in 200 ml. of dimethylformamide. The solution is, after addition of 15.0 g. of 4-methoxy-3-butyl-2,6-dimethyl benzylaldehyde, treated at 10° C. dropwise with a solution of 1.64 g. of sodium in 40 ml. of absolute ethanol. The mixture is subsequently stirred for 12 hours at room temperature, then introduced into 500 ml. of methanol/water 60:40 parts by volume and thoroughly extracted with hexane. The hexane extract is washed with methanol/water 60:40 parts by volume, then with water, dried over sodium sulfate and evaporated. There is obtained 9-(4-methoxy-3-butyl-2,6-dimethyl-phenyl)-3,7-dimethyl-nona-2,4,6,8-tetraen-1-oic acid ethyl ester, which is converted, as described in Example 7, into 9-(4-methoxy-3-butyl-2,6-dimethyl-phenyl)-3,7-dimethyl-nona-2,4,6,8-tetraen-1-oic acid; m.p.: 147°–148° C.

EXAMPLE 62

294 ml. of butyric acid anhydride are treated, after the addition of 2 ml. of concentrated aqueous sulfuric acid, at room temperature with 122 g. of 3,5-dimethyl-phenol. The temperature rises to 40° C. and is then raised to 80° C. The mixture is stirred for 1 hour and diluted with 60 ml. of water and 60 ml. of ethanol, poured onto ice water and twice extracted with 500 ml. of hexane each time. The hexane extract is washed with water, aqueous sodium bicarbonate solution, dried over sodium sulfate and evaporated. There is obtained 1 butyryloxy-3,5-dimethyl-benzene which boils at 123°–125° C./11 mm Hg after rectification.

180 g. of 1-butyryloxy-3,5-dimethyl-benzene are treated at room temperature with 340 g. of aluminium chloride. The mixture is stirred for 4 hours at 90°–95° C., then cooled at 70° C., poured onto ice and 3n aqueous hydrochloric acid and extracted with ether. The ether extract is washed with water to neutral reaction, dried over sodium sulfate and evaporated. There is obtained 2-butyryl-3,5-dimethyl-phenol, which melts at 48°–52° C. after recrystallization from petroleum ether.

10 g. of 2-butyryl-3,5-dimethyl-phenol are dissolved in 100 ml. of glacial acetic acid. After the addition of 3 drops of perchloric acid, the solution is hydrogenated under normal conditions in the presence of 0.5 g. of platinum oxide. After the uptake of 3.0 l. of hydrogen, the hydrogenation is stopped. The catalyst is filtered off. The filtrate is extracted with ether. The ether extract is washed with water to neutral reaction, dried over sodium sulfate and evaporated. There is obtained 2-butyl-3,5-dimethylphenol, which melts at 65°–67° C. after absorption on silica gel, using methylene chloride/hexane 1:1 parts by volume as the eluent.

83 g. of 2-butyl-3,5-dimethyl-phenol are dissolved in 225 ml. of methanol. After the addition of 60 g. of potassium hydroxide in 25 ml. of water, the solution is treated at room temperature with 34.2 g. of methyl iodide. The mixture is heated to boiling under reflux conditions for 3 hours, then cooled, diluted with water and extracted with ether. The ether extract is washed with diluted sodium hydroxide solution, dried over sodium sulfate and evaporated. There is obtained 2-butyl-3,5-dimethyl-anisole, which is purified by absorption on silica gel, using hexane/methylene chloride 70:30 parts by volume as the eluent, before processing further.

5.5 ml. of phosphorous oxychloride are added dropwise while stirring to 4.6 ml. of dimethylformamide. The temperature rises to 30° C. The mixture is treated dropwise with 9.6 g. of 2-butyl-3,5-dimethylanisole, poured onto ice water after the addition of 30 to 35 percent aqueous solution of sodium acetate, stirred for 1 hour and extracted with benzene. The benzene extract is washed with water, dried over sodium sulfate and evaporated. There is obtained 4-methoxy-3-butyl-2,6-dimethyl-benzaldehyde, which is purified by absorption on silica gel, using hexane/methylene chloride 1:1 parts by volume as the eluent, before the condensation with 1-ethoxycarbonyl-2,6-dimethyl-hepta-1,3,5-trien-7-triphenylphosphonium bromide.

EXAMPLE 63

36 g. of 7-formyl-3-methyl-octa-2,4,6-trien-1-oic acid ethyl ester are dissolved in 600 ml. of absolute ethanol. The solution is treated portionwise with 1.8 g. of sodium borohydride. The mixture is stirred for 2 hours at 10° C., then poured onto ice water and 3n aqueous hydrochloric acid and extracted with ether. The ether extract is washed successively with water, a saturated aqueous sodium bicarbonate solution and once more with water, dried over sodium sulfate and evaporated. There is obtained 8-hydroxy-3,7-dimethyl-octa-2,4,6-trien-1-oic acid ethyl ester, which is processed further as follows:

36.5 g. of 8-hydroxy-3,7-dimethyl-octa-2,4,6-trien-1-oic acid ethyl ester are dissolved in 380 ml. of ether. The solution is cooled to 0° C., and after the addition of 3 drops of pyridine treated dropwise with 28.6 g. of phosphorous tribromide in 120 ml. of hexane. The mixture is stirred for 20 minutes at 0° C., then poured onto ice water and extracted with ether. The ether extract is washed successively with water, a saturated aqueous sodium bicarbonate solution and again with water, dried over sodium sulfate and evaporated. There is obtained 8-bromo-3,7-dimethyl-octa-2,4,6-trien-1-oic acid ethyl ester, which is processed as follows:

43.7 g. of 8-bromo-3,7-dimethyl-octa-2,4,6-trien-1-oic acid ethyl ester are dissolved in 500 ml. of benzene and treated with 42.0 g. of triphenylphosphine. The mixture is stirred for 12 hours at room temperature, then cooled at 0° C. The precipitated 1-ethoxycarbonyl-2,6-dimethyl-hepta-1,3,5-trien-7-triphenylphosphonium bromide melts at 193°–194° C.

EXAMPLE 64

In analogy to the procedure given in Example 61:
3,4-dimethoxy-2,6-dimethyl-benzaldehyde is condensed with 1-ethoxycarbonyl-2,6-dimethyl-hepta-1,3,5-trien-7-triphenylphosphonium bromide to produce 9-(3,4-dimethoxy-2,6-dimethyl-phenyl)-3,7-dimethylnona-2,4,6,8-tetraen-1-oic acid ethyl ester which is converted by the procedure of Example 7 to 9-(3,4-dimethoxy-2,6-dimethyl-phenyl)-3,7-dimethyl-nona-2,4,6,8-tetraen-1-oic acid, m.p.: 203°–204° C.

EXAMPLE 65

The 3,4-dimethoxy-2,6-dimethyl-benzaldehyde employed as starting material, can be prepared in a manner analogous to that described in Example 64 by the following sequence:
2,4-dimethylphenol
2,4-dimethyl-6-nitro-phenol
2,4-dimethyl-6-nitro-anisole
2,4-dimethyl-6-amino-anisole
2,4-dimethyl-6-hydroxy-anisole
2,4-dimethylveratrole.

EXAMPLE 66

In analogy to the procedure given in Example 9-(4-methoxy-2,3,6-trimethyl-phenyl)-3,7-dimethyl-nona-2,4,6,8-tetraen-1-oic acid chloride is reacted with methyl-amine to produce 9-(4-methoxy-2,3,6-trimethyl-phenyl)-3,7-dimethyl-nona-2,4,6,8-tetraen-1-oic acid methyl amide, m.p. 206° C.;

9-(4-methoxy-2,3,6-trimethyl-phenyl)-3,7-dimethyl-nona-2,4,6,8-tetraen-1-oic acid chloride is reacted with isopropyl amine to produce 9-(4-methxy-2,3,6-trimethyl-phenyl)-3,7-dimethyl-nona-2,4,6,8-tetraen-1-oic acid isopropyl amide, m.p. 200° C.;

9-(4-methoxy-2,3,6-trimethyl-phenyl)-3,7-dimethyl-nona-2,4,6,8-tetraen-1-oic acid chloride is reacted with butyl amide to produce 9-(4-methoxy-2,3,6-trimethyl-phenyl)-3,7-dimethyl-nona-2,4,6,8-tetraen-1-oic acid butyl amide, m.p. 178° C.; and 9-(4-methoxy-2,3,6-trimethyl-phenyl)-3,7-dimethyl-nona-2,4,6,8-tetraen-1-oic acid chloride is reacted with hexylamide to produce 9-(4-methoxy-2,3,6-trimethyl-phenyl)-3,7-dimethyl-nona-2,4,6,8-tetraen-1-oic acid hexylamide, m.p. 157°–158° C.

EXAMPLE 67

9-(4-Methoxy-2,3,6-Trimethylphenyl)-3,7-Dimethyl-2,4,6,8-Nonatetraen-1-ol

In a 5-liter, round bottom flask provided with a stirrer, low temperature thermometer, an inlet for dry nitrogen, a gas outlet, and a dropping funnel connected to a mineral oil bubbler, were placed 150 g (0.436 moles) of 9-(4-methoxy-2,3,6-trimethylphenyl)-3,7-dimethyl-2,4,6,8-nonatetraenoic acid ethyl ester and 800 ml of toluene. The contents were stirred until the solids had dissolved, then by means of a dry ice bath, the internal temperature was lowered to −60° C., at which temperature 780 ml of a 25% solution of diisobutylaluminum (DIBAL) hydride in toluene (1.155 moles) was added dropwise. The initially yellow solution or suspension gradually deepened in color and after all the DIBAL had been added, the reaction mixture consisted of a clear, somewhat viscous deep red orange solution. After stirring for one hour, the cooling bath was lowered and the internal temperature allowed to rise to −40° C., at which temperature, 50 ml of a 50% aqueous methanol solution was added dropwise with intermittent cooling so that when the addition was complete the temperature was approximately 10° C. At this point, 140 ml of a saturated solution of sodium sulfate was added dropwise. Allowing the temperature to gradually rise to 25° C. Toward the end of the addition, aluminum hydroxide began to precipitate with the evolution of heat. After stirring for a few minutes, 800 ml of chloroform was added and the suspension stirred for ten minutes. The precipitate was removed by filtration on a twelve-inch Buchner funnel through a layer of filter aid, then washed four times with 500 ml portions of chloroform. The combined filtrates were washed successively with 600 ml of water, 600 ml of water containing 10 ml of 3N hydrochloric acid, 600 ml of saturated sodium bicarbonate solution, and 600 ml of water, then dried over anhydrous sodium sulfate. Distillation of the solvent in the rotary evaporator left 130-145 g of a crystalline residue. To this was added one liter of hexane and the suspension stirred vigorously until the aggregates had been dispersed; any material adhering to the walls was scraped off. The yellow crystalline precipitate was recovered by filtration, washed twice with sufficient hexane to cover the filter cake, then dried in vacuo first at 12-15 mm (water pump), then at 0.5 mm until the weight was constant. The yield of product was 119-123 g, m.p. 127.5°-129.5° C.

Distillation of the hexane from the filtrate and washings in the rotary evaporator left a residue of 12-15 g that crystallized very slowly, and yielded approximately 6-8 g of high quality material.

EXAMPLE 68

Methyl Ether of 9-(4-Methoxy-2,3,6-Trimethylphenyl)-3,7-Dimethyl-2,4,6,8-nonatetraene-1-ol In a 5-l, round bottom flask flushed with nitrogen provided with a stirrer, thermometer, gas inlet tube, reflux condenser topped by a gas outlet connected to a mineral oil bubbler, and a six-inch length of Gooch tubing were placed 156 g (0.5 moles) of 9-(4-methoxy-2,3,6-trimethylphenyl)-3,7-dimethyl-2,4,6,8-nonatetraene-1-ol, 564 g (4 moles) of methyl iodide and 2.5 l of tetrahydrofuran. To the stirred solution, at 20°-25° C., 24 g (1.0 moles) of sodium hydride were gradually added over a period of about one hour from a 500 ml Erlenmeyer flask connected through the Gooch tubing. The yellow solution became turbid and assumed a brownish tint. Within a few minutes the temperature rose to 28° C. but was maintained at 25° C. by external cooling. After 2.5 hours, the reaction vessel was cooled to 10° C. by an ice bath and the excess sodium hydride decomposed by the dropwise addition of 50% aqueous methanol. The solvent was then distilled in the rotary evaporator leaving a partially crystalline residue that was dissolved in 500 ml of benzene and transferred to a separatory funnel where it was washed successively with three 500-ml portions of saturated sodium bicarbonate solution and once with water containing a little sodium sulfate. To the benzene solution, 100 mg of butylated hydroxy toluene (BHT) was added, together with anhydrous sodium sulfate, then the solvent distilled in a rotary evaporator leaving 172 g of an orange syrup.

This syrup together with another 167 g of a similarly prepared lot was dissolved in 750 ml of warm hexane and filtered. The stirred solution was allowed to crystallize at room temperature for approximately one hour, then the crystallization completed at 0° C., all under nitrogen. The yellow orange crystalline product was recovered by filtration (nitrogen) and washed twice with hexane. After drying, first at 10-15 mm, and then at 0.5 mm to constant weight, 266 g (81%) of product was obtained m.p. 67.5°-69.5° C.

EXAMPLE 69

The n-Butyl Ether of 9-(4-Methoxy-2,3,6-Trimethylphenyl)-3,7-Dimethyl-2,4,6,8-Nonatetraen-1-ol Under nitrogen, 6.0 of 9-(4-methoxy-2,3,6-trimethylphenyl)-3,7-dimethyl-nonatetraen-1-ol, (0.0192 moles) was dissolved in 150 ml of tetrahydrofuran containing 28.05 g of n-butyliodide in a 250 ml, round bottom, flask provided with a stirrer, thermometer, nitrogen inlet tube, and an opening for the addition of a solid, through which was added 0.92 g of sodium hydride. The mixture was stirred for 48 hours, then cooled, and the excess hydride decomposed by the cautious addition of methanol. The mixture was then diluted with 500 ml of water and extracted with three 50-ml portions of ether. After drying over magnesium sulfate, the solvent was distilled in the rotary evaporator and the residue taken up in ten ml of hexane. On addition of ten ml of methanol, 2.65 g of crystals of the starting material, m.p. 107°-112° C. were obtained. The filtrate after removal of the solid, was freed of solvent and the residue was chromatographed on 200 g of silica gel. From the fraction eluted with 50% ether in hexane was obtained 2.6 g of a solid, which after recrystallization from methanol afforded 1.5 g of deep yellow crystals, m.p. 52°-54° C.

We claim:

1. A compound of the formula:

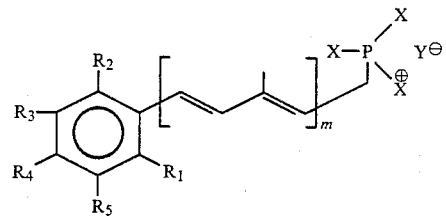

wherein m is an integer from 0 to 1: $R_1$ and $R_2$ are lower alkyl: $R_3$ is hydrogen, lower alkyl, lower alkoxy, lower alkenyloxy, or nitro: $R_4$ is lower alkoxy and $R_5$ is hydrogen, lower alkyl, lower alkenyl, lower alkoxy, lower alkenyloxy: X is aryl: and Y is an anion of an inorganic or organic acid.

2. The compound of claim 1 wherein said compound is 4-methoxy-2,6-dimethyl-benzyl-triphenylphosphonium chloride.

3. The compound of claim 1 wherein said compound is 4-methoxy-2,3,5,6-tetramethyl-benzyl-triphenylphosphonium chloride.

4. The compound of claim 1 wherein said compound is 4-methoxy-3-allyl-2,6-dimethyl-benzyl-triphenylphosphonium chloride.

5. The compound of claim 1 wherein said compound is 4-methoxy-3-nitro-2,6-dimethyl-benzyl-triphenylphosphonium chloride.

6. The compound of claim 1 wherein said compound is 5-(4-methoxy-2,3,6-trimethyl-phenyl)-3-methyl-penta-2,4-dien-1-triphenylphosphonium bromide.

7. The compound of claim 1 wherein said compound is 4-ethoxy-2,3,6-trimethyl-benzyl-triphenylphosphonium chloride.

8. The compound of claim 1 wherein said compound is 4-isopropoxy-2,3,6-trimethyl-benzyl-triphenylphosphonium chloride.

9. The compound of claim 1 wherein one of $R_3$ or $R_5$ is nitro.

10. The compound of claim 1 wherein one of $R_3$ or $R_5$ is lower alkenyloxy.

* * * * *